US011357758B2

(12) United States Patent
Gentzsch et al.

(10) Patent No.: US 11,357,758 B2
(45) Date of Patent: Jun. 14, 2022

(54) EPITHELIAL CELL SPHEROIDS AND METHODS OF MAKING AND USING THE SAME

(71) Applicant: The University of North Carolina at Chapel Hill, Chapel Hill, NC (US)

(72) Inventors: Martina Gentzsch, Hurdle Mills, NC (US); Scott Randell, Durham, NC (US); Nancy L. Quinney, Durham, NC (US); Susan Boyles, Chapel Hill, NC (US); Jennifer Guimbellot, Mountain Brook, AL (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1076 days.

(21) Appl. No.: 15/440,720

(22) Filed: Feb. 23, 2017

(65) Prior Publication Data

US 2017/0242033 A1 Aug. 24, 2017

Related U.S. Application Data

(60) Provisional application No. 62/298,792, filed on Feb. 23, 2016.

(51) Int. Cl.
| | | |
|---|---|---|
| *G01N 33/50* | (2006.01) | |
| *G01N 33/68* | (2006.01) | |
| *A61K 35/24* | (2015.01) | |
| *G01N 11/02* | (2006.01) | |
| *A61B 5/145* | (2006.01) | |
| *A61B 5/1477* | (2006.01) | |
| *A61K 31/443* | (2006.01) | |
| *A61K 31/47* | (2006.01) | |
| *C09B 67/00* | (2006.01) | |

(52) U.S. Cl.
CPC ............ *A61K 31/443* (2013.01); *A61K 31/47* (2013.01); *G01N 33/5044* (2013.01); *G01N 33/6893* (2013.01); *A61B 5/1477* (2013.01); *A61B 5/14507* (2013.01); *A61B 5/14539* (2013.01); *A61K 35/24* (2013.01); *C09B 68/00* (2013.01); *G01N 11/02* (2013.01)

(58) Field of Classification Search
CPC ...... A61K 31/443; A61K 31/47; A61K 35/24; G01N 33/5044; G01N 33/6893; G01N 11/02; A61B 5/14507; A61B 5/14539; A61B 5/1477; C09B 68/00
See application file for complete search history.

(56) References Cited

U.S. PATENT DOCUMENTS

2015/0011420 A1* 1/2015 Beekman ........... G01N 33/5026
506/10

FOREIGN PATENT DOCUMENTS

| WO | WO 2012/131000 A1 | 10/2012 |
| WO | WO 2013/093812 A2 | 6/2013 |

OTHER PUBLICATIONS

Pedersen et al. American Journal of Physiology—Lung Cellular and Molecular Physiology, vol. 276, No. 1, 1999, pp. L75-L80.*
Agu et al. International Journal of Pharmaceutics, vol. 193, Issue 2, Jan. 5, 2000, pp. 219-226.*
Agu et al. Pharmaceutical Research, vol. 16, Issue 9, Sep. 1999, pp. 1380-1385.*
Willems et al. Journal of Cystic Fibrosis, vol. 3, 2004, pp. 53-54.*
StemCell Technologies, Technical Bulletin "Sphere Culture of Differentiated HBECs with PneumaCult™—ALI" published Feb. 2015 (Year: 2015).*
Castillon et al. (Laboratory Investigation, vol. 82, No. 8: 989-98, 2002 (Year: 2002).*
Chaudhry et al. "CFTR Rescue Affects Secreted Mucins and Mucus" Poster Presented at the 29th Annual North American Cystic Fibrosis Conference (1 page) (Oct. 8-10, 2015).
Cholon et al. "Pharmacological Rescue of Mutant CFTR: Exploring Mutant-Specific Therapies" Marsico Lung Institute and Cystic Fibrosis Research Center, Poster Presented at the 29th Annual North American Cystic Fibrosis Conference (1 page) (Oct. 8-10, 2015).
Dekkers et al. "A functional CFTR assay using primary cystic fibrosis intestinal organoids" Nature Medicine, 19 (7):939-947 (2013).
Knowles et al. "Mutations in RSPH1 Cause Primary Ciliary Dyskinesia with a Unique Clinical and Ciliary Phenotype" American Journal of Respiratory and Critical Care Medicine, 189(6):707-717 (2014).
Okiyoneda et al. "Mechanism-based corrector combination restores DeltaF508-CFTR folding and function" Nature Chemical Biology, 9(7):444-454 (2013).
Sisson et al. "All-digital image capture and whole-field analysis of ciliary beat frequency" Journal of Microscopy, 211 (Pt 2):103-111 (2003) (Abstract only).

* cited by examiner

*Primary Examiner* — Kimberly Ballard
*Assistant Examiner* — Stacey N MacFarlane
(74) *Attorney, Agent, or Firm* — Myers Bigel, P.A.

(57) ABSTRACT

Provided are epithelial cell spheroids including spheroids that have apical membranes and cilia that face towards the interior core of the spheroid and spheroids that have apical membranes and cilia that face away from the interior core of the spheroid. Also provided methods of making and using such spheroids.

20 Claims, 22 Drawing Sheets

Inward facing spheres, grown in matrigel

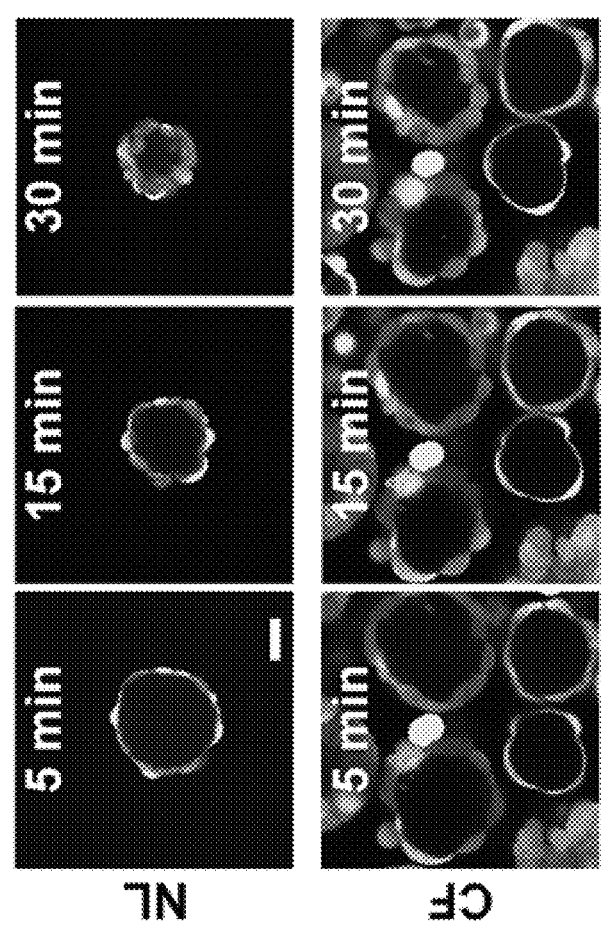
FIG. 7A  FIG. 7B  FIG. 7C

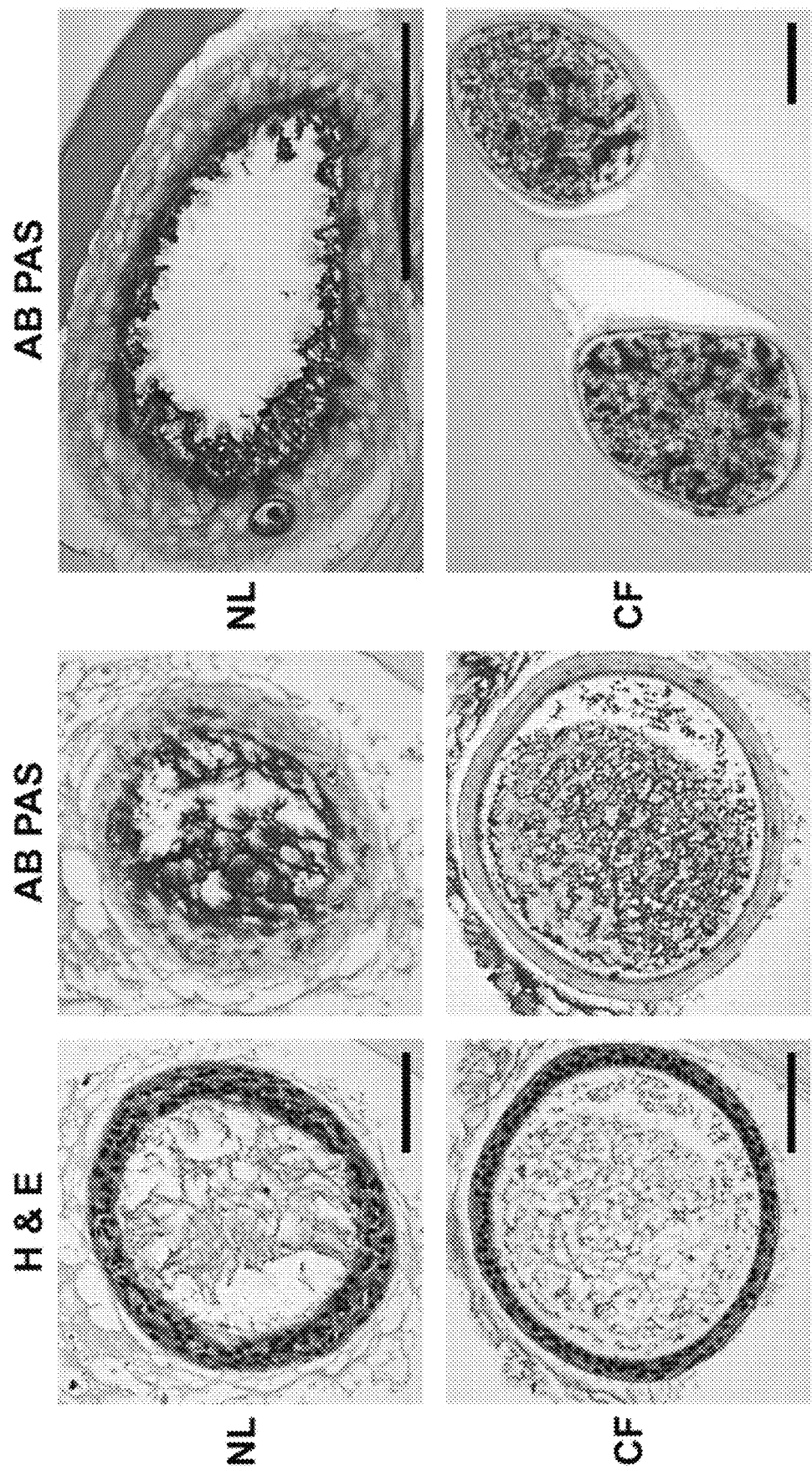

EPITHELIAL CELL SPHEROIDS AND METHODS OF MAKING AND USING THE SAME

RELATED APPLICATION INFORMATION

This application claims the benefit of and priority to U.S. Provisional Patent Application Ser. No. 62/298,792, filed Feb. 23, 2016, the disclosure of which is incorporated herein by reference in their entirety.

STATEMENT OF GOVERNMENT SUPPORT

This invention was made with government support under Grant No. 2 P30 DK065988 awarded by the National Institutes of Health. The government has certain rights in the invention.

FIELD

The present invention generally relates to epithelial cell spheroids and methods of making and using the same.

BACKGROUND OF THE INVENTION

Channelopathies, such as cystic fibrosis, are diseases caused by a disturbed function of an ion channel subunit and/or a protein that regulates an ion channel subunit and can affect numerous people. For example, cystic fibrosis (CF) affects ~30,000 people in the U.S., ~70,000-100,000 worldwide, and is caused by a mutation in the cystic fibrosis transmembrane conductance regulator gene (CFTR). Assays to facilitate the development of ion channel modulators, such as, for example, CFTR modulators, for specific rare mutations and for identifying the most effective existing ion channel modulator or modulator combination treatments for their specific mutation would be useful since over 2,000 mutations have been identified. Furthermore, even CF patients with the same genotype showed variable responses to CFTR-targeting drugs in clinical trials. Therefore, assays for personalized testing of small molecule compounds that restore ion channel function may be advantageous.

SUMMARY OF THE INVENTION

According to an aspect of the present invention, provided is a method of determining an ion channel response to a chemical and/or biological compound, the method comprising: contacting a spheroid comprising epithelial cells with the chemical and/or biological compound; and, responsive to the spheroid being contacted with the chemical and/or biological compound, identifying a physiological response of the spheroid, thereby determining the ion channel response to the chemical and/or biological compound.

In some embodiments, the ion channel response to the chemical and/or biological compound may indicate the ion channel response in a subject if the subject was administered the chemical and/or biological compound. In some embodiments, the spheroid comprises epithelial cells derived from the subject.

A further aspect of the present invention provides a method of assessing efficacy of a chemical and/or biological compound for the treatment of a channelopathy (e.g., cystic fibrosis (CF)) in a subject, the method comprising: contacting a spheroid comprising epithelial cells derived from the subject with the chemical and/or biological compound; and, responsive to the spheroid being contacted with the chemical and/or biological compound, identifying a physiological response of the spheroid, thereby assessing efficacy of the chemical and/or biological compound for the treatment of the channelopathy in the subject.

Another aspect of the present invention provides a method of treating a subject with a channelopathy (e.g., cystic fibrosis (CF)), the method comprising: contacting a spheroid comprising epithelial cells derived from the subject with the chemical and/or biological compound; responsive to the spheroid being contacted with the chemical and/or biological compound, identifying a physiological response of the spheroid; determining a treatment regimen based on the physiological response; and treating said subject according to the treatment regimen.

A further aspect of the present invention provides a method of detecting a disorder exhibiting aberrant mucus properties in a subject comprising: contacting a spheroid comprising epithelial cells derived from the subject with a chemical and/or biological compound; responsive to the spheroid being contacted with the chemical and/or biological compound, identifying a physiological response of the spheroid (e.g., swelling, shrinking, cilia activity, etc.); and, responsive to identifying the physiological response, determining that the physiological response indicates that the subject has a disorder exhibiting aberrant mucus properties.

Another aspect of the present invention provides a method of detecting a channelopathy in a subject comprising: contacting a spheroid comprising epithelial cells derived from the subject with a chemical and/or biological compound; responsive to the spheroid being contacted with the chemical and/or biological compound, identifying a physiological response of the spheroid (e.g., swelling, shrinking, cilia activity, etc.); and, responsive to identifying the physiological response, determining that the subject has a result that indicates the channelopathy.

According to further embodiments of the present invention, provided is a method of preparing a spheroid comprising epithelial cells, the method comprising: culturing epithelial cells in a medium in a container with an ultra low attachment surface, thereby preparing the spheroid from the cultured epithelial cells.

Another aspect of the present invention includes a cellular aggregate comprising epithelial cells, wherein the cellular aggregate is in the form of a spheroid. In some embodiments, the spheroid comprises an interior core and an exterior surface, and a plurality of the epithelial cells have apical membranes and cilia that face towards the interior core of the spheroid. In some embodiments, the spheroid comprises an interior core and an exterior surface, and a plurality of the epithelial cells have apical membranes and cilia that face away from the interior core of the spheroid.

BRIEF DESCRIPTION OF THE DRAWINGS

FIG. 2A shows that CFTR from ΔF508/ΔF508

HBE is efficiently rescued by VX-809. FIG. 2B shows that CFTR from N1303K/W1282X is not rescued by VX-809.

FIG. 3A shows that CFTR from G551D/ΔF508 HBE is potentiated similarly by acute and chronic treatment with 5 μM VX-770. FIG. 3B shows that S1251N has a robust response to VX-809 with low concentrations of VX-770 (1 μM) that is decreased with higher concentrations of VX-770 (5 μM). In addition, the ΔΔG values (−8.1 kcal/mol for G551D, and -0.8 kcal/mol for S1251N) further suggest that S1251N is less stable than G551D.

FIGS. 7A-7E show that 3D spheroid cultures from nasal and bronchial tissue (nasospheres and bronchospheres) can form in two orientations. When CFTR is active, outside-facing spheres shrink, and inside-facing spheres swell. FIGS. 7A-7D, nasospheres. FIG. 7E, bronchospheres.

FIG. 9A shows representative short-circuit current (Isc) traces measured in Ussing chambers. FIG. 9B shows isc responses to amiloride, forskolin, VX-770, and CFTR-Inh172 (N=3). FIG. 9C shows MUCSAC Western blotting. FIG. 9D shows the intensity of the MUCSAC signal is diminished in VX-770-rescued cultures.

FIGS. 10A-10D show that bronchospheres produce mucus, and when CFTR function is lost, ciliary beat frequency is diminished. Primary normal (NL) and P67L/ΔF508 CF bronchial spheres grown in a collagen-containing semi-solid matrix (e.g., matrigel) with the apical surface facing the inside (FIG. 10A). Sections were stained with H & E or AB PAS (Bars=100 μm). AB PAS staining of NL and CF bronchospheres at different magnifications. (Bars=100 μm) (FIG. 10B). Cilia of bronchosphere (Bar=5 μm) (FIG. 10C). NL and ΔF508/ΔF508 CF bronchospheres with beating cilia were analyzed to determine cilia beat frequency (CBF) (FIG. 10D). The graph shows average CBF from NL and CF spheres (N=6). CBF in NL spheres (10.4±1.4 Hz) was significantly faster than in CF spheres (6.5±0.9 Hz) (P=0.0002).

DETAILED DESCRIPTION

Figure 1:
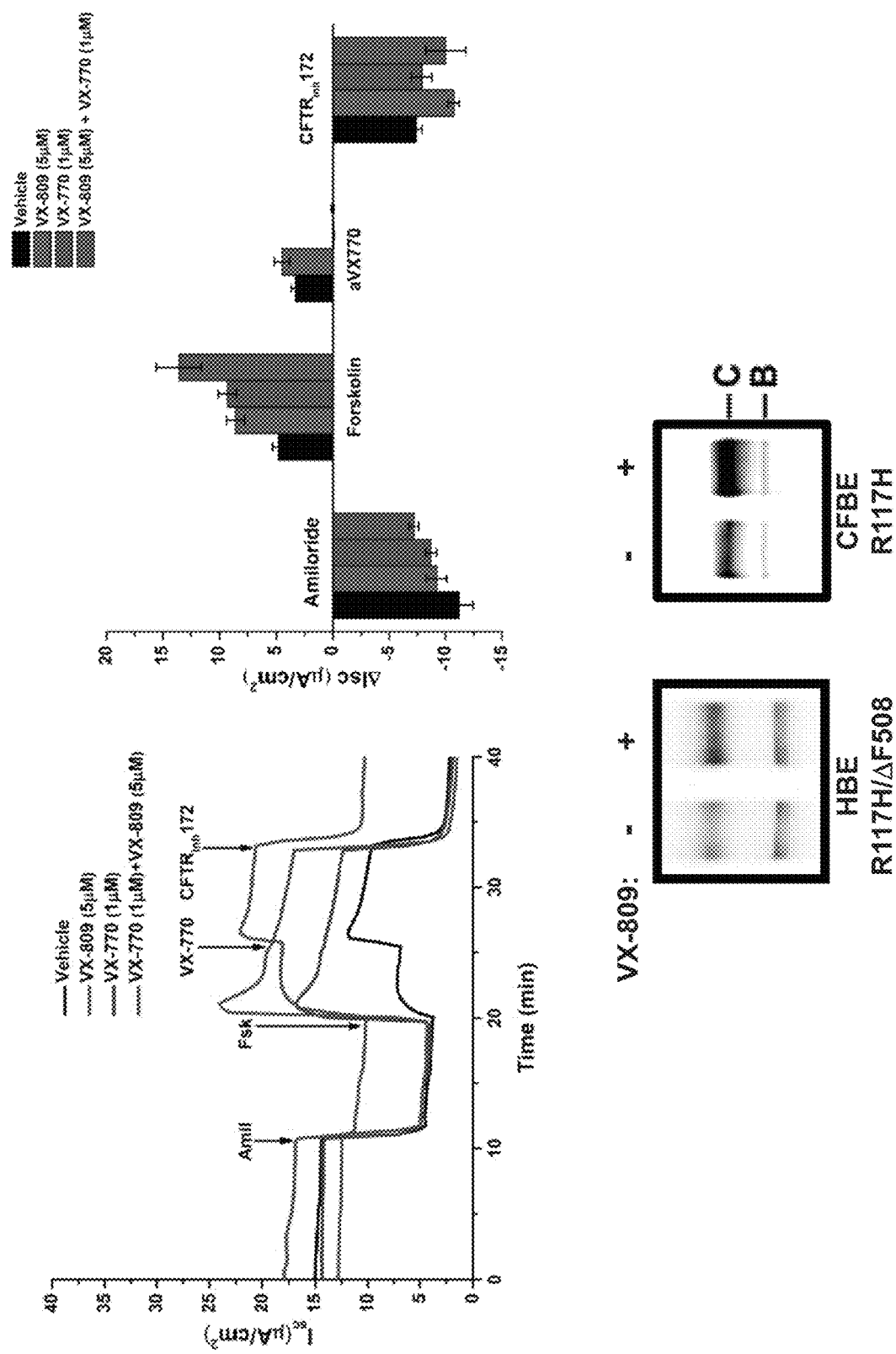
FIG. 1 depicts R117H, a CFTR conductance mutation. CFTR in R117H/ΔF508 HBE is efficiently rescued by either VX-809 or VX-770 alone, and rescue is further enhanced with combination treatment. The forskolin response is highest with VX-809 plus a low dose of VX-770 (1 μM). R117H expressed in the cell line, CFBE41o-, is corrected by VX-809, indicating that R117H is also a processing mutation. The ΔΔG (1.03 kcal/mol) provides further evidence that this mutation is destabilized.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value, such as an amount or concentration and the like, is meant to refer to variations of up to ±20% of the specified value, such as, but not limited to, +10%, ±5%, ±1%, ±0.5%, or even ±0.1% of the specified value, as well as the specified value. For example, "about X" where X is the measurable value, is meant to include X as well as variations of ±20%, +10%, ±5%, ±1%, +0.5%, or even ±0.1% of X. A range provided herein for a measurable value may include any other range and/or individual value therein.

Provided according to embodiments of the present invention is a cellular aggregate comprising epithelial cells, wherein the cellular aggregate is in the form of a spheroid. The cellular aggregate and/or spheroid of the present invention refers to a multicellular structure (i.e., a cellular structure of two or more cells). In some embodiments, the cellular aggregate and/or spheroid may be a microtissue. The terms "cellular aggregate" and "spheroid" are used interchangeably herein. The spheroid may be a prolate spheroid or an oblate spheroid. The center or middle of a spheroid may be hollow or may comprise one or more cells. In some embodiments, the center of a spheroid is hollow.

A spheroid of the present invention can have any suitable width, length, thickness, and/or diameter. In some embodiments, a spheroid may have a width, length, thickness, and/or diameter in a range from about 10 μm to about 50,000 μm, or any range therein, such as, but not limited to, from about 10 μm to about 900 μm, about 100 μm to about 700 μm, about 300 μm to about 600 μm, about 400 μm to about 500 μm, about 1,000 μm to about 10,000 μm, about 2,000 to about 50,000 μm, about 25,000 μm to about 40,000 μm, or 3,000 μm to about 15,000 μm. In some embodiments, a spheroid may have a width, length, thickness, and/or diameter of about 50 μm, 100 μm, 200 μm, 300 μm, 400 μm, 500 μm, 600 μm, 700 μm, 800 μm, 900 μm, 1,000 μm, 5,000 μm, 10,000 μm, 20,000 μm, 30,000 μm, 40,000 μm, or 50,000 μm. In some embodiments, a plurality of spheroids are generated, and each of the spheroids of the plurality may have a width, length, thickness, and/or diameter that varies by less than about 20%, such as, for example, less than about 15%, 10%, or 5%.

The spheroid may comprise any suitable epithelial cell. In some embodiments, the spheroid may comprise nasal, bronchial, alveolar (e.g., alveolar type II (ATII)), sweat duct/gland, mammary, intestinal, colon, ocular (e.g., lens and/or retinal), circulatory endothelium, peritoneal mesothelium, pleural cavity, pericardial cavity, esophageal epithelium, gingival, vaginal, corneal, oral, kidney tubule, ovarian, bronchial, mammary gland, sweat gland, salivary gland, gastric, intestinal, uterine, tracheal, fallopian tube, ocular conjunctiva, urethra, pharynx, small intestine, large intestine, gall bladder, thyroid follicles, anus, vas deferens, lymph vessel, skin, endometrium and/or cervix epithelial cell(s). In some embodiments, the spheroid comprises airway epithelial cells. In some embodiments, the spheroid comprises epithelial cells that have been conditionally reprogrammed. In some embodiments, the spheroid comprises nasal epithelial cells and is referred to as a nasosphere. In some embodiments, the spheroid comprises bronchial epithelial cells and is referred to as a bronchosphere. In some embodiments, the spheroid comprises alveolar epithelial cells and is referred to as an alveolosphere.

The epithelial cells in a spheroid may be obtained and/or derived from a mammal (e.g., a human, rat, mouse, dog, horse, cat, cow, pig, horse, etc.). In some embodiments, the epithelial cells in a spheroid may be obtained and/or derived from a subject for whom a method and/or test is being performed with the spheroid.

The cells in a spheroid may have a particular orientation. In some embodiments, the spheroid may comprise an interior core and an exterior surface, and at least a portion of the epithelial cells have apical membranes and, if present, cilia that face towards the interior core of the spheroid (i.e., an inside-facing spheroid). In some embodiments, greater than 50% (e.g., 55%, 60%, 65%, 70%, 75%, 80%, 85%, 90%, 95%, 98%, 99%, or 100%) of the epithelial cells in the spheroid have apical membranes and, if present, cilia that face towards the interior core of the spheroid. In some embodiments, the spheroid may comprise an interior core and an exterior surface, and at least a portion of the epithelial cells have apical membranes and, if present, cilia that face away from the interior core of the spheroid (i.e., an outside-facing spheroid). In some embodiments, greater than 50% (e.g., 55%, 60%, 65%, 70%, 75%, 80%, 85%, 90%, 95%, 98%, 99%, or 100%) of the epithelial cells in the spheroid have apical membranes and, if present, cilia that face away from the interior core of the spheroid. In some embodiments, the interior core of an inside-facing spheroid or outside-facing spheroid may be hollow (i.e., may not comprise cells). In some embodiments, the epithelial cells do not comprise cilia (i.e., are non-ciliated cells). When the epithelial cells are ciliated, the cilia may be oriented in the same direction as the apical membrane (e.g., both facing towards the interior core of the spheroid or both facing away from the interior core of the spheroid).

According to some embodiments of the present invention, provided are methods of using a spheroid of the present invention. In some embodiments, a method of determining, evaluating, and/or measuring an ion channel response to a chemical and/or biological compound may be provided. In some embodiments, a method of determining, evaluating, and/or measuring an ion channel response to a chemical and/or biological compound may determine, evaluate and/or measure the impact of an ion channel response. In some embodiments, determining, evaluating, and/or measuring the impact of an ion channel response may quantify a proxy parameter for the ion channel response, but not the direct response.

A method of determining, evaluating, and/or measuring an ion channel response to a chemical and/or biological compound may comprise contacting a spheroid of the present invention with the chemical and/or biological compound, and, responsive to the spheroid being contacted with the chemical and/or biological compound, identifying a physiological response of the spheroid, thereby determining, evaluating, and/or measuring the ion channel response to the chemical and/or biological compound. In some embodiments, the contacting step may be carried out and/or performed in culture. In some embodiments, a method of the present invention may be a high-throughput method. In some embodiments, a method of the present invention may comprise obtaining epithelial cells from a subject and/or preparing the spheroid The physiological response of the spheroid may indicate and/or demonstrate how an ion channel present in the spheroid responds to the chemical and/or biological compound (e.g., increasing and/or decreasing the flow of ions across an ion channel). Thus, the physiological response may indicate (e.g., be predictive of) and/or demonstrate how an ion channel in a subject (e.g., the same ion channel or one similar to the ion channel in the spheroid) may respond when the subject is administered the chemical and/or biological compound. In some embodiments, the ion channel response to the chemical and/or biological compound may indicate (e.g., be predictive of) and/or demonstrate an ion channel response, such as, for example, an ion channel response in a subject if the subject was administered the chemical and/or biological compound. For example, in some embodiments, the physiological response of the spheroid may demonstrate and/or indicate (e.g., be predictive of) how an ion channel in a subject may respond if the subject was administered the chemical and/or biological compound.

In some embodiments, the spheroid used in a method of the present invention may comprise epithelial cells derived and/or obtained from the subject. The subject may have or may be suspected to have a defect and/or mutation in an ion channel. In some embodiments, the subject may have a channelopathy. In some embodiments, the subject may not have a channelopathy. In some embodiments, the subject may have or may be suspected to have a disease or disorder that disrupts at least one function of an ion channel subunit and/or a disease or disorder that disrupts at least one protein that regulates an ion channel and/or subunit thereof. In some embodiments, the subject may have or may be suspected to have a disease or disorder that affects mucus production and/or a mucus property in the subject. In some embodiments, the subject may have or may be suspected to have cystic fibrosis, asthma, chronic obstructive pulmonary disorder, primary ciliary dyskinesia, Job's disease (trachea), Best's Disease (lens epithelium, retinal), a pancreatic disease, a kidney disorder, a pancreatic disease (e.g., type2 diabetes, hypoglycemia), a kidney disorder (e.g., Butter's syndrome, polycystic kidney disease, Dent's disease), a heart disease (e.g., cardiac arrhythmias, long Q/T syndrome), a gastrointestinal disorder (e.g., IBS, Crohn's disease, gastroparesis, chronic diarrhea, gastroesophageal reflux disease (GERD), congenital absence of the vas deferens (CAVD), and/or a disease associated with decreased epithelial sodium channel (ENaC) activity (e.g., Liddle syndrome, type I pseudohypoaldosteronism (PHA-I), cystic fibrosis, and high-altitude pulmonary edema (nasal, bronchial, kidney)).

In some embodiments, the subject is human. In some embodiments, the subject is non-human, such as, for example a livestock and/or domestic animal. The livestock and/or domestic animal may have or may be suspected to have a channelopathy. In some embodiments, the livestock and/or domestic animal may have or may be suspected to have bovine respiratory disease (BRD), bovine pulmonary hypertension (BPH), high altitude pulmonary hypertension (HAPH), acute bovine pulmonary emphysema and edema (ABPEE), porcine muscle hypertrophy (MH), and/or equine muscle ion channelopathies (MIC).

In some embodiments, a method of the present invention may be used to understand the physiology of the subject (e.g., human or non-human). In some embodiments, a method of the present invention may be used in selective breeding strategies and/or to determine whether or not to breed the subject with another.

A spheroid of the present invention, which may be used in a method of the present invention, may comprise any ion channel. In some embodiments, the spheroid may comprise a cystic fibrosis transmembrane conductance regulator (CFTR), epithelial sodium channel (ENaC), a potassium channel, and/or calcium-activated chloride channel (CaCC). A method of the present invention may determine, evaluate, measure, and/or identify a physiological response of a spheroid and provide an indication (e.g., prediction) and/or demonstrate how an ion channel, such as, for example, a CFTR, ENaC, a potassium channel, and/or CaCC, responds to a chemical and/or biological compound. In some embodiments, a method of the present invention may comprise inhibiting the activity of at least one ion channel, which may allow and/or provide for the activity of at least one different ion channel to be determined in response to contact with a chemical and/or biological compound. For example, a method of the present invention may inhibit the activity of ENaC, a potassium channel, and/or CaCC in a spheroid and determine the physiological response of a spheroid to provide an indication and/or demonstrate how a CFTR responds to a chemical and/or biological compound.

Any suitable physiological response of the spheroid may be determined, evaluated, measured, and/or identified in a method of the present invention. In some embodiments, 1, 2, 3, 4, or more physiological response(s) of the spheroid may be determined, evaluated, measured, and/or identified in a method of the present invention. In some embodiments, the physiological response of the spheroid may be a change in morphology for the spheroid. The method may comprise determining a change in morphology for the spheroid, which may include estimating at least one morphology parameter prior to contacting the spheroid with a chemical and/or biological compound, estimating the at least one morphology parameter after contacting the spheroid with the chemical and/or biological compound, and calculating the difference between the at least one morphology parameter prior to and after contacting the spheroid with the chemical and/or biological compound to provide the change in morphology for the spheroid. In some embodiments, the physiological response of the spheroid may be the spheroid shrinking or swelling in response to contact with a chemical and/or biological compound. Morphology of the spheroid may be determined using any methods known to those of skill in the art, such as, but not limited to, quantifying eccentricity and/or cross sectional area.

In some embodiments, the physiological response of the spheroid may be a change in volume for the spheroid. The method may comprise determining a change in volume for the spheroid, which may include estimating a first volume prior to contacting the spheroid with a chemical and/or biological compound, estimating a second volume after contacting the spheroid with the chemical and/or biological compound, and calculating the difference between the first volume and the second volume to provide the change in volume for the spheroid. In some embodiments, the physiological response of the spheroid may be the spheroid shrinking or swelling in response to contact with a chemical and/or biological compound.

In some embodiments, the physiological response of the spheroid may be the production of a mucus by the spheroid and/or identifying a change in mucus produced by the spheroid. Identifying a change in the mucus may comprise identifying an increase or decrease in mucus production. In some embodiments, identifying a change in the mucus may comprise identifying a change in the viscoelasticity of the mucus after contacting the spheroid with a chemical and/or biological compound compared to the viscoelasticity of the mucus prior to contacting the spheroid with the chemical and/or biological compound. In some embodiments, identifying a change in the mucus may comprise identifying a change in the pH of the mucus and/or a change in the composition of the mucus after contacting the spheroid with a chemical and/or biological compound compared to the pH and/or composition of the mucus prior to contacting the spheroid with the chemical and/or biological compound. In some embodiments, a change in the mucus solids concentration may be detected and/or identified.

In some embodiments, the physiological response of the spheroid may be comprise determining a change in cilia activity for the spheroid after contacting the spheroid with a chemical and/or biological compound compared to cilia activity for the spheroid prior to contacting the spheroid with the chemical and/or biological compound. A change in cilia activity can be determined by measuring cilia dynamics. Methods for measuring and/or evaluating cilia activity are known to those of skill in the art, see, e.g., Quinn S P, et al. "Novel use of differential image velocity invariants to categorize ciliary motion defects." *Proceedings of the Biomedical Science and Engineering Conference (BSEC)* 2011 and Quinn, Shannon P. et al. "Automated Identification of Abnormal Respiratory Ciliary Motion in Nasal Biopsies" *Science translational medicine* 7.299 (2015): 299ra124. PMC. Web. 21 Feb. 2017. For example, determining a change in cilia activity for the spheroid may comprise determining a change in cilia dynamics. In some embodiments, determining a change in cilia dynamics for the spheroid may comprise estimating a first cilia dynamics parameter prior to contacting the spheroid with a chemical and/or biological compound, estimating a second cilia dynamics parameter after contacting the spheroid with the chemical and/or biological compound, and calculating the difference between the first cilia dynamics parameter and the second cilia dynamics parameter to provide the change in cilia dynamics for the spheroid. The first and/or second cilia dynamics parameter may be an average cilia dynamics parameter.

In some embodiments, determining a change in cilia activity for the spheroid may comprise determining a change in cilia beat frequency. In some embodiments, determining a change in cilia beat frequency for the spheroid may comprise estimating a first cilia beat frequency prior to contacting the spheroid with a chemical and/or biological compound, estimating a second cilia beat frequency after contacting the spheroid with the chemical and/or biological compound, and calculating the difference between the first cilia beat frequency and the second cilia beat frequency to provide the change in cilia beat frequency for the spheroid. The first and/or second cilia beat frequency may be an average cilia beat frequency.

In some embodiments, the physiological response of the spheroid in response to contact with a chemical and/or biological compound may be an indication of the efficacy of the chemical and/or biological compound in modulating at least one ion channel, such as, for example, an ion channel in a subject. "Modulate," "modulating," "modulation," and grammatical variations thereof as used herein refer to an increase or reduction in a property (e.g., an increase or decrease in activity) of an ion channel compared to the property of the ion channel in the absence of the chemical and/or biological compound. As used herein, the terms "increase," "increases," "increased," "increasing" and similar terms indicate an elevation in a property (e.g., the activity of an ion channel, such as opening or closing) of at least about 5%, 10%, 20%, 30%, 40%, 50%, 60%, 70%, 80%, 90%, 100%, 150%, 200%, 300%, 400%, 500% or more compared to the property in the absence of the chemical and/or biological compound. As used herein, the terms "reduce," "reduces," "reduced," "reduction" and similar terms refer to a decrease in a property (e.g., the activity of an ion channel, such as opening or closing) of at least about 5%, 10%, 20%, 30%, 40%, 50%, 60%, 70%, 75%, 80%, 85%, 90%, 95%, 97% or more compared to the property in the absence of the chemical and/or biological compound. In some embodiments, the reduction may result in little or essentially no detection of the property, such as, e.g., an insignificant amount, e.g., less than about 10% or even 5%.

In some embodiments, an increase in cilia activity (e.g., cilia beat frequency) in a spheroid in response to contact with a chemical and/or biological compound may be an indication and/or may demonstrate that the chemical and/or biological compound may be effective in modulating a pharmacological response in a subject. In some embodiments, an increase in cilia activity (e.g., cilia beat frequency) in a spheroid in response to contact with a chemical and/or biological compound may be an indication and/or may demonstrate that the chemical and/or biological compound may be effective in modulating at least one ion channel in a subject.

The physiological response of a spheroid in response to contact with a chemical and/or biological compound may be an indication of and/or may demonstrate the activity of an ion channel. For example, the physiological response of the spheroid in response to contact with a chemical and/or biological compound may be an indication and/or may demonstrate that at least one ion channel function and/or response is increased. In some embodiments, the physiological response of the spheroid in response to contact with a chemical and/or biological compound may be an indication and/or may demonstrate that at least one ion channel function and/or response is restored. In some embodiments, the physiological response of the spheroid in response to contact with a chemical and/or biological compound may be an indication and/or may demonstrate that at least one ion channel function and/or response is decreased. In some embodiments, one or more (e.g., 1, 2, 3, 4, 5, or more) ion channel function(s) and/or response(s) may be determined, identified, and/or evaluated and these function(s) and/or response(s) may be for the same and/or different ion channels. For example, one or more function(s) and/or response(s) of a single ion channel may be determined, identified, and/or evaluated. Alternatively or in addition, one or more function(s) and/or response(s) of two or more different ion channels may be determined, identified, and/or evaluated.

In some embodiments, the physiological response of a spheroid in response to contact with a chemical and/or biological compound may be an indication and/or may demonstrate that a chemical and/or biological compound may increase at least one ion channel function and/or response upon administering the chemical and/or biological compound to a subject, such as, e.g., the subject whose cells were used to prepare the spheroid. In some embodiments, the physiological response of a spheroid in response to contact with a chemical and/or biological compound may be an indication and/or may demonstrate that a chemical and/or biological compound may decrease at least one ion channel function and/or response upon administration to a subject, such as, e.g., the subject whose cells were used to prepare the spheroid.

In some embodiments, the physiological response of a spheroid in response to contact with a chemical and/or biological compound may be an indication and/or may demonstrate that a chemical and/or biological compound may activate at least one ion channel upon administration to the subject, such as, e.g., the subject whose cells were used to prepare the spheroid. In some embodiments, the physiological response of the spheroid in response to contact with a chemical and/or biological compound may be an indication and/or may demonstrate that a chemical and/or biological compound may deactivate at least one ion channel upon administration to the subject, such as, e.g., the subject whose cells were used to prepare the spheroid.

According to some embodiments, the physiological response of a spheroid in response to contact with a chemical and/or biological compound may be an indication and/or may demonstrate the severity of a disease and/or disorder that affects at least one ion channel function, response, and/or mucus property in a subject, such as, e.g., the subject whose cells were used to prepare the spheroid. The physiological response may be used to determine or select a therapeutic or treatment regimen for the subject.

In some embodiments, a spheroid of the present invention may not be prepared from cells of a subject in order to indicate and/or demonstrate how the subject and/or an ion channel in the subject may respond to a chemical and/or biological compound upon administering the chemical and/or biological compound to the subject. For example, the spheroid may be prepared from cells that include an abnormal and/or malfunctioning ion channel and/or an ion channel with at least one mutation and the subject may have the same or a similar functioning ion channel and/or an ion channel with the same or a similar mutation.

The chemical and/or biological compound may be any suitable compound, such as, for example, an organic compound, a small molecule compound (e.g., a small molecule organic compound), a protein, an antibody, an oligonucleotide (e.g., DNA and/or RNA), a gene therapy vehicle (e.g., a viral vector) and any combination thereof. One or more (e.g., 1, 2, 3, 4, 5, or more) chemical and/or biological compounds may be used in a method of the present invention. For example, a method of the present invention may comprise contacting a spheroid of the present invention with two or more different chemical and/or biological compounds. In some embodiments, a method of the present invention may modulate an ion channel function and/or activity in a spheroid indirectly, such as, for example, by contacting a spheroid of the present invention with a gene therapy vehicle (e.g., a viral vector).

In some embodiments, the chemical and/or biological compound may be an ion channel modulator. An "ion channel modulator" as used herein refers to a chemical and/or biological compound that increases or decreases a function and/or activity of an ion channel. For example, an ion channel modulator may increase the flow of ions across the ion channel and/or decrease the flow of ions across the ion channel. In some embodiments, the ion channel modulator may be an ion channel blocker and/or an ion channel opener. The ion channel modulator may be a CFTR modulator, such as, e.g., a CFTR potentiator, a CFTR corrector, a CFTR stabilizer, or a CFTR amplifier. In some embodiments, the chemical and/or biological compound may be an ion channel modulator, but may modulate the ion channel function and/or activity differently depending on the ion channel and/or subject. For example, the ion channel modulator may increase an ion channel activity for some subjects, such as, e.g., those without a mutation in the ion channel, but may decrease the ion channel activity for other subjects, such as, e.g., those with a mutation in the ion channel.

In some embodiments, a method of the present invention may utilize a spheroid prepared from cells obtained and/or derived from a subject. In some embodiments, the subject may have a channelopathy, such as, for example, CF. The physiological response of the spheroid (e.g., shrinking or swelling) may be an indication and/or demonstrate that a chemical and/or biological compound (e.g., an ion channel modulator) may be effective in treating a channelopathy, such as, for example, CF, in the subject.

According to some embodiments, a method of the present invention may access, determine, and/or evaluate efficacy of a chemical and/or biological compound for the treatment of a channelopathy, such as, e.g., CF, in a subject. The method may comprise contacting a spheroid comprising epithelial cells derived and/or obtained from the subject with the chemical and/or biological compound and, responsive to the spheroid being contacted with the chemical and/or biological compound, identifying a physiological response of the spheroid, thereby assessing, determining, and/or evaluating efficacy of the chemical and/or biological compound for the treatment of the channelopathy in the subject.

In some embodiments, a method of the present invention may treat a subject with a channelopathy, such as, e.g., CF. The method may comprise contacting a spheroid comprising epithelial cells derived and/or obtained from the subject with a chemical and/or biological compound, responsive to the spheroid being contacted with the chemical and/or biological compound, identifying a physiological response of the spheroid, determining or selecting a therapeutic and/or treatment regimen based on the physiological response, and treating the subject with the therapeutic and/or according to the treatment regimen. "Treatment regiment" as used herein may include a therapeutic administration schedule (e.g., one or more therapeutics to administer) and/or dosing schedule (e.g., amounts and/or time for administering one or more therapeutics).

The terms "treat", "treating", and grammatical variants thereof, as used herein in reference to treating a subject, refer to any type of treatment that imparts a benefit to a subject and may mean that the severity of the subject's condition is reduced, at least partially improved or ameliorated and/or that some alleviation, mitigation or decrease in at least one clinical symptom associated with the condition is achieved and/or there is a delay in the progression of the disease or disorder, e.g., channelopathy. In some embodiments, the severity of a subject's condition may be reduced compared to the severity of the condition in the absence of a method of the present invention. A method of the present invention may provide the total absence of the disease, disorder, and/or clinical symptom in the subject. A method of the present invention may also provide partial treatment, such as relieving and/or reducing the effects and/or severity of the disease, disorder, and/or clinical symptom in the subject and/or delaying the progression and/or onset of the disease, disorder, and/or clinical symptom compared to what would occur in the absence of the method of the present invention.

In some embodiments, a method of the present invention may determine and/or identify a treatment effective amount of a therapeutic or a therapeutic combination for treating a subject. A "treatment effective" amount as used herein is an amount that is sufficient to treat (as defined herein) the subject. Those skilled in the art will appreciate that the therapeutic effects need not be complete or curative, as long as some benefit is provided to the subject. The method may comprise contacting a spheroid comprising epithelial cells derived and/or obtained from the subject with the therapeutic or therapeutic combination, responsive to the spheroid being contacted with the therapeutic or therapeutic combination, identifying a physiological response of the spheroid, determining and/or identifying that the physiological response is treatment effective. Determining and/or identifying that the physiological response is treatment effective may comprise determining the extent of the physiological response and/or comparing the physiological response to at least one control response. In some embodiments, the therapeutic or therapeutic combination may comprise a chemical and/or biological compound.

In some embodiments, a method of the present invention may detect a disorder exhibiting aberrant mucus properties in a subject. The method may comprise contacting a spheroid comprising epithelial cells derived and/or obtained from the subject with a chemical and/or biological compound, responsive to the spheroid being contacted with the chemical and/or biological compound, identifying a physiological response of the spheroid (e.g., swelling, shrinking, cilia activity, etc.), and responsive to identifying the physiological response, determining that the physiological response indicates that the subject has a disorder exhibiting aberrant mucus properties. In some embodiments the subject may have a channelopathy. The method may further comprise comparing the physiological response to at least one control response, and, responsive identifying the physiological response and comparing the physiological response to the at least one control response, determining that the physiological response indicates that the subject has a disorder exhibiting aberrant mucus properties.

According to some embodiments, a method of detecting a channelopathy in a subject may be provided. The method may comprise contacting a spheroid comprising epithelial cells derived and/or obtained from the subject with a chemical and/or biological compound, responsive to the spheroid being contacted with the chemical and/or biological compound, identifying a physiological response of the spheroid (e.g., swelling, shrinking, cilia activity, etc.), and, responsive to identifying the physiological response, determining that the subject has a result that indicates the channelopathy. The result may be the physiological response of the spheroid. The method may further comprise comparing the physiological response to at least one control response, and, responsive to identifying the physiological response and comparing the physiological response to the at least one control response, determining that the subject has a result that indicates the channelopathy.

According to some embodiments, a method of the present invention may comprise immobilizing a spheroid (e.g., an AMI and/or AMO spheroid). In some embodiments, a spheroid may be incubated with an antibody that detects an epitope (e.g., extracellular epitope) on the spheroid. For example, for a spheroid, such as, e.g., a nasosphere and/or bronchosphere, an antibody that detects an extracellular mucin domain of transmembrane mucins (e.g., Muc1 antibody binding to extracellular Muc1 domain) on the spheroid may be used to immobilize the spheroid. The antibody may be bound or attached to a substrate prior to or after binding to a spheroid. For example, after incubation with an antibody, a spheroid may be washed and may subsequently be contacted and/or added to a Protein A, G, A/G, and/or L coated microplate and/or dish, such as those commercially available. Antibodies bound to the spheroid may be captured by Protein A, G, A/G, and/or L that is tethered and/or attached to the microplate and/or dish. In some embodiments, the microplate and/or dish may be washed, which may remove unbound spheroids. In some embodiments, immobilized spheroids may be used in a method that includes determining a change in morphology (e.g., shrinking or swelling) and/or cilia activity.

A method of preparing a spheroid may be provided according to some embodiments of the present invention. In some embodiments, a method of preparing a spheroid comprising epithelial cells may comprise culturing epithelial cells in a medium in a container with an ultra low attachment surface, thereby preparing the spheroid from the cultured epithelial cells. The method may comprise obtaining the epithelial cells from a subject, optionally a subject that has or is suspected to have a channelopathy. The cultured cells may form a spheroid that comprises an interior core and an exterior surface, wherein a plurality of the epithelial cells have apical membranes and optionally cilia that face away from the interior core of the spheroid (i.e., apical membrane out (AMO) or outside-facing spheroid). In some embodiments, an AMO spheroid may be collected from cell culture media 2-7 days (e.g., 2, 3, 4, 5, 6, or 7 days) after beginning the culturing of epithelial cells.

In some embodiments, a method of preparing an AMO spheroid may comprise preparing and/or forming the spheroid from ex-vivo tissue and epithelial sheets in containers (e.g., plates) that prevent attachment of cells to the surface (e.g. ultra-low attachment plates) or hanging drop plates, without a matrix-based substrate. In some embodiments, the spheres form by aggregation of cells that develop at the tissue or sheet, and spheres are released into the media. In some embodiments, the formation of a spheroid (e.g., an AMO spheroid) is most effective in a minimal volume of media that is cell- and tissue-specific with avoidance of attachment to a surface. In some embodiments, an AMO spheroid may be cultured from passaged cells, such as, for example, by using a high ratio of cells to media in ultra-low attachment container (e.g. 400,000-1 Million HBE cells in up to 400 µL media incubated in a 16 mm diameter ultra-low attachment dish). In some embodiments, AMO spheroid polarization results from different ion channels present at the apical and basolateral cell membranes with cilia oriented to the outside.

In some embodiments, the method of preparing the spheroid may comprise isolating and/or expanding adherent epithelial cells. Prior to forming the spheroid, the epithelial cells may be conditionally reprogrammed. In some embodiments, the conditionally reprogrammed cells may be cultured and may form a spheroid that comprises an interior core and an exterior surface, and a plurality of the epithelial cells have apical membranes and optionally cilia that face towards the interior core of the spheroid. (i.e., an apical membrane in (AMI) or inside-facing spheroid). In some embodiments, an AMI spheroid may be formed in Matrigel from conditionally reprogrammed expanded epithelial cells.

In some embodiments, an AMI spheroid may be prepared and/or formed from conventional (primary) and/or conditionally reprogrammed cells that are mechanically and/or enzymatically dissociated. These cells may be mixed in a matrix solution at cold temperatures (e.g., 4-10° C.). The matrix solution may become a semi-solid as it warms to 37° C., which may promote the formation of AMI spheroids. In some embodiments, AMI spheroid polarization results from different ion channels present at the apical and basolateral cell membranes with apical membrane and cilia oriented to the inside.

A method of the present invention may comprise culturing cells and/or a spheroid. Culturing may be carried out using methods known to those knowledgeable in the field. In some embodiments, cells and/or a spheroid may be cultured for any desired period of time, such as, but not limited, hours, days, weeks, or months. In some embodiments, cells and/or a spheroid may be cultured for about 1, 2, 3, 4, 5, 6, or 7 days, or about 1, 2, 3, 4, 5, 6, 7, 8, 9, 10, or 11 or more weeks.

Cell culture media suitable for the methods of the present invention are known in the art and include, but are not limited to, BEGM™ Bronchial Epithelial Cell Growth medium, Dulbecco's Modified Eagle's Medium (DMEM), Dulbecco's Modified Eagle's Medium high glucose (DMEM-H), McCoy's 5A Modified Medium, RPMI, Ham's media, Medium 199, mTeSR, and so on. The cell culture medium may be supplemented with additional components such as, but not limited to, vitamins, minerals, salts, growth factors, carbohydrates, proteins, serums, amino acids, attachment factors, cytokines, growth factors, hormones, antibiotics, therapeutic agents, buffers, etc. The cell culture components and/or conditions may be selected and/or changed during the methods of the present invention to enhance and/or stimulate certain cellular characteristics and/or properties. Examples of seeding methods and cell culturing methods are described in U.S. Pat. Nos. 5,266,480, 5,770,417, 6,537,567, and 6,962,814 and Oberpenning et al. "De novo reconstitution of a functional mammalian urinary bladder by tissue engineering" *Nature Biotechnology* 17:149-155 (1999), which are incorporated herein by reference in their entirety.

The cell seeding and/or culturing may be carried out in a sterile environment using equipment and methods known in the art. In some embodiments, the temperature of the cell seeding is from about 0° C. to 15° C., such as, for example, from about 0° C. to about 10° C. or about 0° C. to about 4° C., or any range and/or value (e.g., 0, 1, 2, 3, 4, 5, 6, 7, 8, 9, 10, 11, 12, 13, 14, or 15° C.) therein. In some embodiments of the present invention, the temperature of the culturing environment is from about 25° C. to about 40° C. or any range therein, such as from about 30° C. to about 40° C. or from about 35° C. to about 40° C. In some embodiments, the temperature of the cell culturing environment is about 37° C. The cell culturing environment may be at atmospheric pressure, reduced pressure (e.g., vacuumized pressure), high pressure, and/or any combination thereof. In some embodiments, the pressure of the cell culturing environment may be atmospheric pressure. In some embodiments, the cell culturing steps may be carried out in an atmosphere of from about 1% to about 20% carbon dioxide ($CO_2$) or any range therein, such as from about 5% to about 10% or from about 5% and about 15% $CO_2$. In some embodiments, cell culturing may be carried out in an atmosphere of from about 5% to about 10% $CO_2$. Other gases, such as, but not limited to, nitrogen and/or oxygen, may be added to the cell seeding and/or culturing atmosphere. In some embodiments, one or more gases may be used to obtain and/or maintain the desired atmosphere (e.g., to maintain the desired oxygen and/or carbon dioxide levels).

According to some embodiments of the present invention, a method of determining if a chemical and/or biological compound is an ion channel modulator may be provided. The method may comprise contacting a spheroid comprising epithelial cells with the chemical and/or biological compound and, responsive to the spheroid being contacted with the chemical and/or biological compound, identifying a physiological response of the spheroid, thereby determining if the chemical and/or biological compound is an ion channel modulator. If no physiological response is identified, then the chemical and/or biological compound may not be an ion channel modulator. In some embodiments, when there is no physiological response identified, the chemical and/or biological compound may not be an ion channel modulator for the particular ion channels present in the spheroid. In some embodiments, if a physiological response is identified, then the chemical and/or biological compound may be an ion channel modulator.

Provided according to some embodiments may be an ex vivo assay and/or method for evaluating, identifying, and/or determining the cellular response to a chemical and/or biological compound, such as, for example, an ion channel modulator. In some embodiments, the assay and/or method may be personalized for a subject, thereby the assay and/or method may determine and/or indicate how the chemical and/or biological compound may act in a subject and/or the response the chemical and/or biological compound may have when administered to a subject. In some embodiments, the assay and/or method may determine CFTR activity and/or if the chemical and/or biological compound modulates CFTR activity and/or if the chemical and/or biological compound may modulate CFTR activity in a subject. In some embodiments, identifying a modulator that restores an ion channel function, such as, e.g., CFTR function in individuals with CFTR mutations or acquired CFTR dysfunction, may increase and/or improve an outcome in a subject, such as, for example, their lung function, decrease exacerbation rates, and increase life expectancy. In some embodiments, the assay and/or method may accelerate individualization of drug therapies, and may avoid delays and/or health risks that may be associated with trial and error approaches. In some embodiments, the assay and/or method may identify a therapeutic or therapeutic combination for a particular ion channel mutation, such as, e.g., a CFTR mutation. In some embodiments, the assay and/or method may identify a therapeutic or therapeutic combination that may not be effective for a particular ion channel mutation, such as, e.g., a CFTR mutation.

EXAMPLES

Example 1

Pharmacological Rescue of Mutant CFTR: Exploring Mutant-Specific Therapies

A major goal in CF therapy is to reproduce the success of potentiator, ivacaftor (VX-770), with G551D CF patients for all CF patients. Combination therapy using the corrector, lumacaftor (VX-809), with VX-770 was predicted to benefit patients homozygous for the misprocessing mutation, ΔF508, but our studies with ΔF508/ΔF508 human bronchial epithelial (HBE) cultures chronically treated with these compounds showed a decrease in CFTR function. We tested these compounds for rescue of rare CF mutations by Ussing chamber and Western blot analyses. HBE cells from CF patients carrying various mutations had dissimilar responses to VX-809 and VX-770, even when grouped in same class. Furthermore, cells from patients with identical CFTR mutations may show different drug responses. We used conditionally reprogrammed cells (CRC) to expand supplies of HBE and human nasal epithelial cells with defined CFTR mutations. We also assessed CFTR function in a physiologically relevant ex vivo assay using 3D spheroid cultures prepared from bronchial and nasal tissues. These bronchospheres and nasospheres allow detection of acute volume changes in response to CFTR activation. The ultimate goal is to utilize personalized approaches to test different combinations of compounds to develop optimal treatment strategies for each CF patient.

CFTR mutations have been broken down into several different classes. Class I mutations, for example, G542X, W1282X and R553X, are defective in synthesis in which no functional CFTR is produced. Class II mutations, for example, ΔF508 and N1303K, are defective in processing, i.e., protein folding and trafficking, and are not transported to the cell surface or are transported in reduced amounts. Class III mutations, for example, G551D, S1251N, G551S and G1349D, are defective in regulation of CFTR, which no longer opens in response to channel agonists. Class IV mutations, for example, R117H, R334W and R347P, are defective in chloride ion conductance. Class V mutations, for example, 3849+10 kb C→T, 2789G→A and A455E, are reduced in amount of functional CFTR produced. Finally, Class VI mutations result in an increase in the turnover of CFTR at the cell surface.

Results

R117H is a conductance mutation. CFTR in R117H/ΔF508 HBE is efficiently rescued by either VX-809 or VX-770 alone, and rescue is further enhanced with combination treatment. The forskolin response is highest with VX-809 plus a low dose of VX-770 (1 μM). R117H expressed in the cell line, CFBE41o-, is corrected by VX-809, indicating that R117H is also a processing mutation. The ΔΔG (1.03 kcal/mol) provides further evidence that this mutation is destabilized (FIG. 1).

Figure 2A:
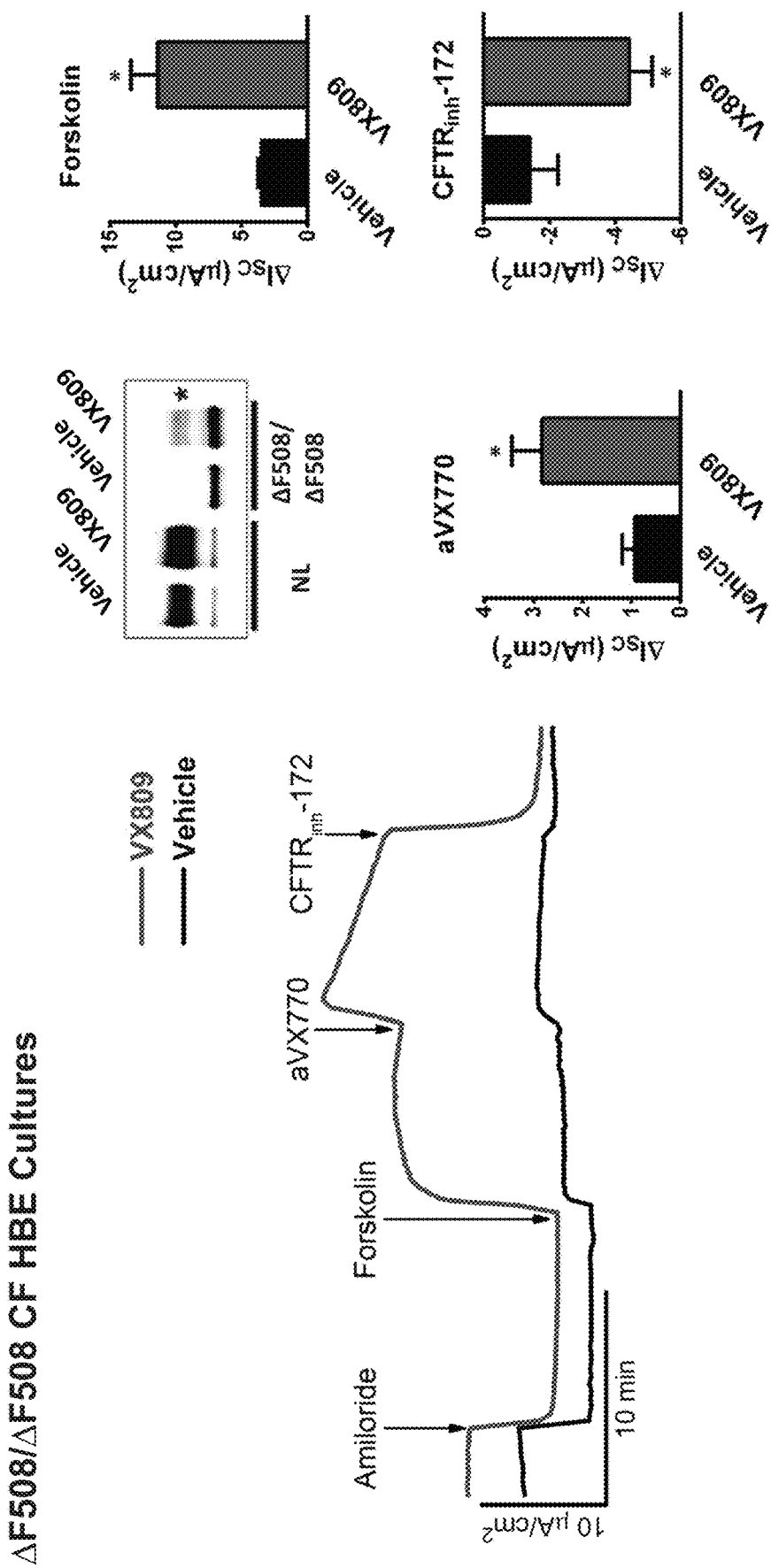
FIGS. 2A and 2B show that ΔF508 and N1303K are both CFTR processing mutations, but respond differently to VX-809.
Figure 2B:
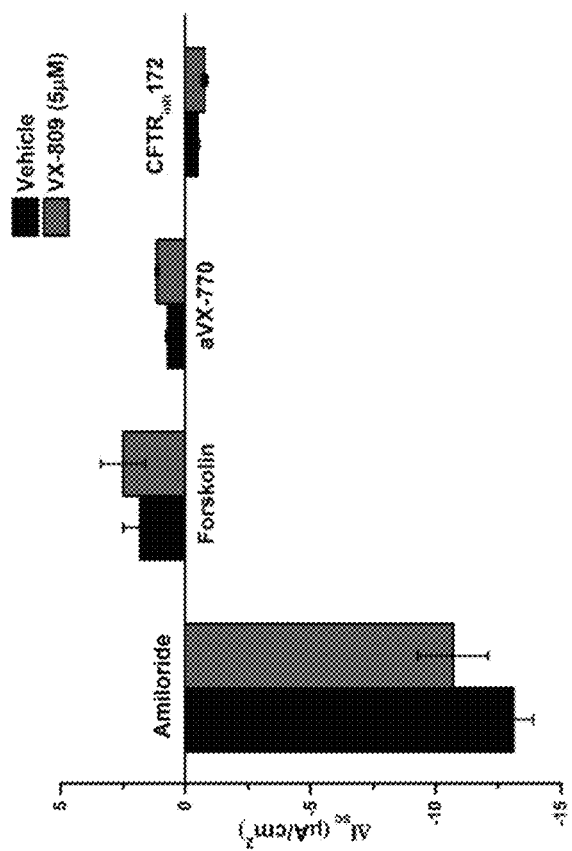
Figure 2B:
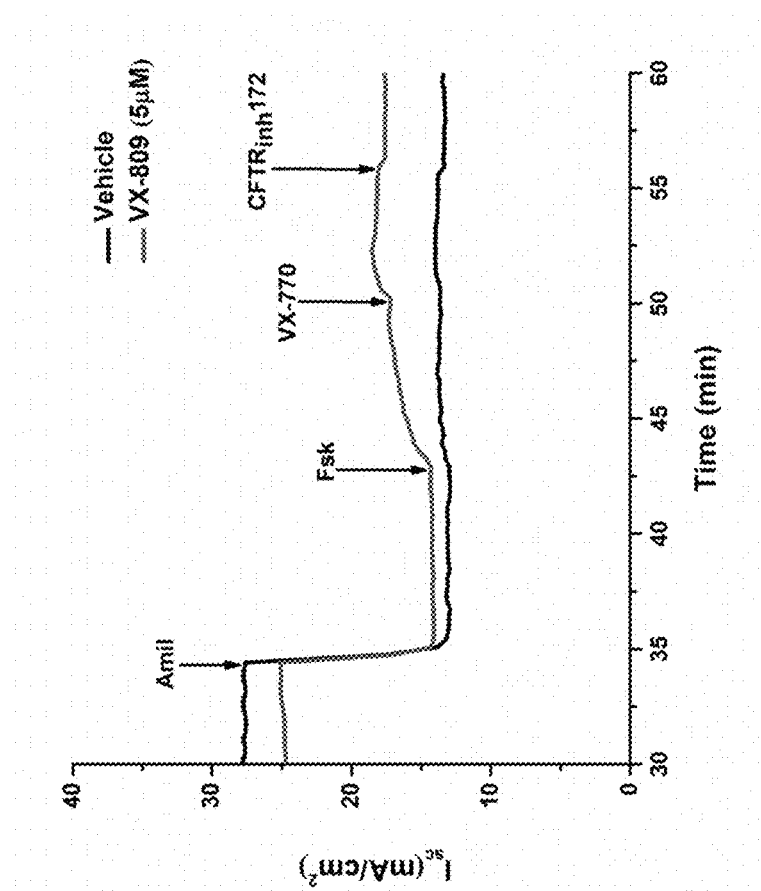

CFTR mutants ΔF508 and N1303K are both processing mutations but respond differently to VX-809. CFTR from ΔF508/ΔF508 HBE (FIG. 2A) is efficiently rescued by VX-809 while CFTR from N1303K/W1282X (FIG. 2B) is not.

Figure 3A:
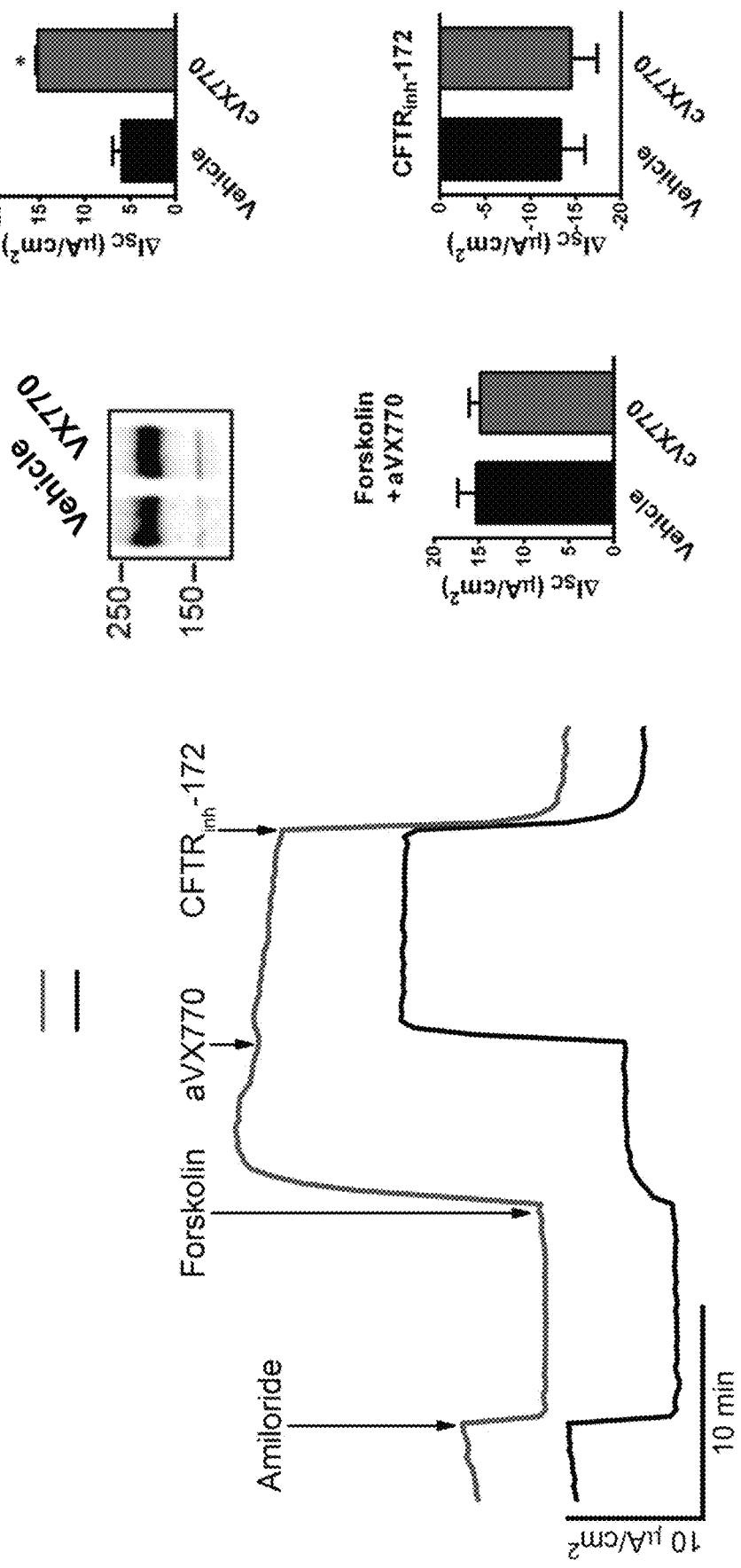
FIGS. 3A and 3B show that G551D and S1251N are both CFTR gating mutations, but respond differently to VX-770.
Figure 3B:
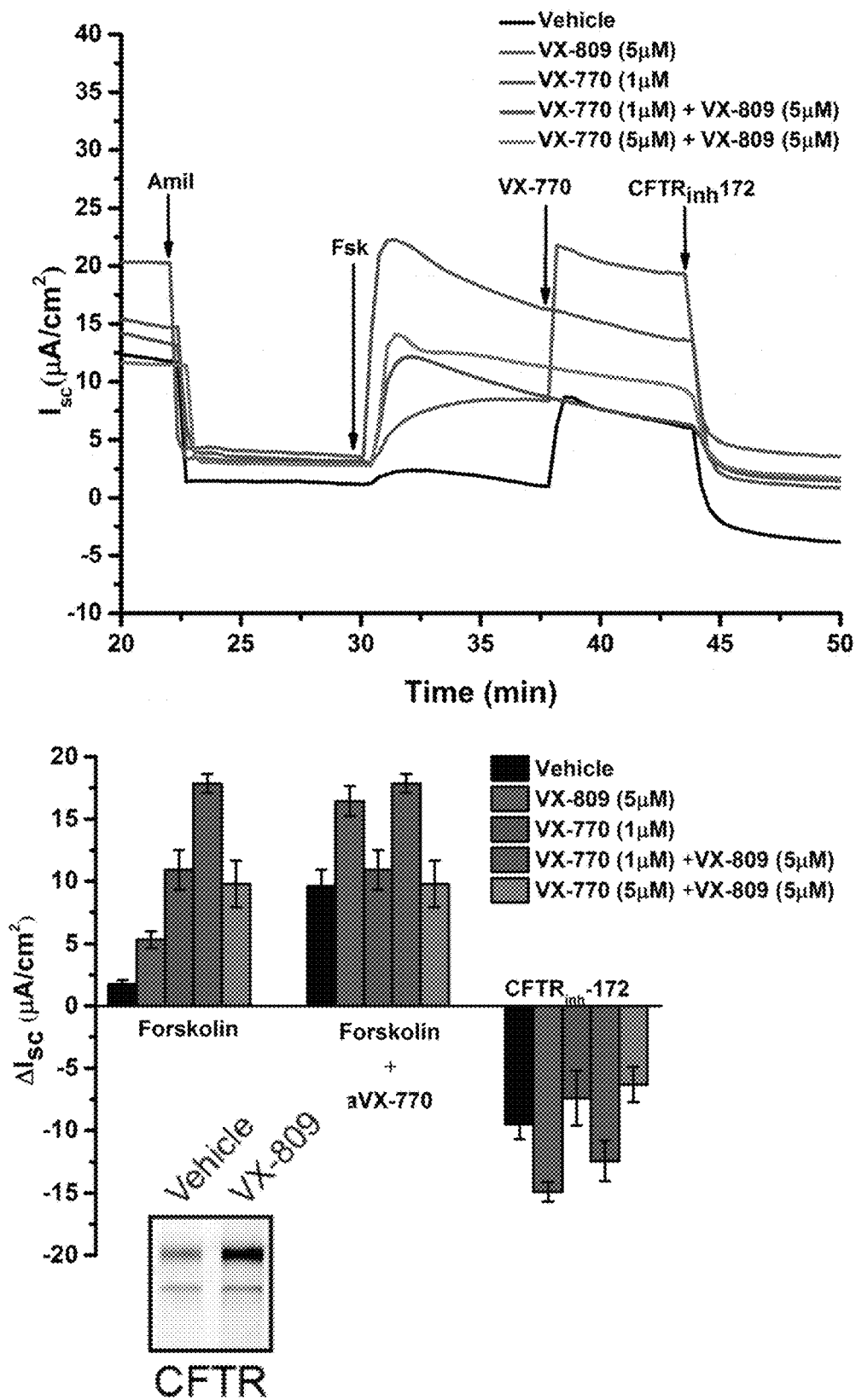

G551D and S1251N are both gating mutations but respond differently to VX-770. CFTR from G551D/ΔF508 HBE (FIG. 3A) is potentiated similarly by acute and chronic treatment with 5 μM VX-770; however, 51251N (FIG. 3B) has a robust response to VX-809 with low concentrations of VX-770 (1 μM) that is decreased with higher concentrations of VX-770 (5 μM). In addition, the ΔΔG values (−8.1 kcal/mol for G551D, and -0.8 kcal/mol for S1251N) further suggest that S1251N is less stable than G551D.

Figure 4:
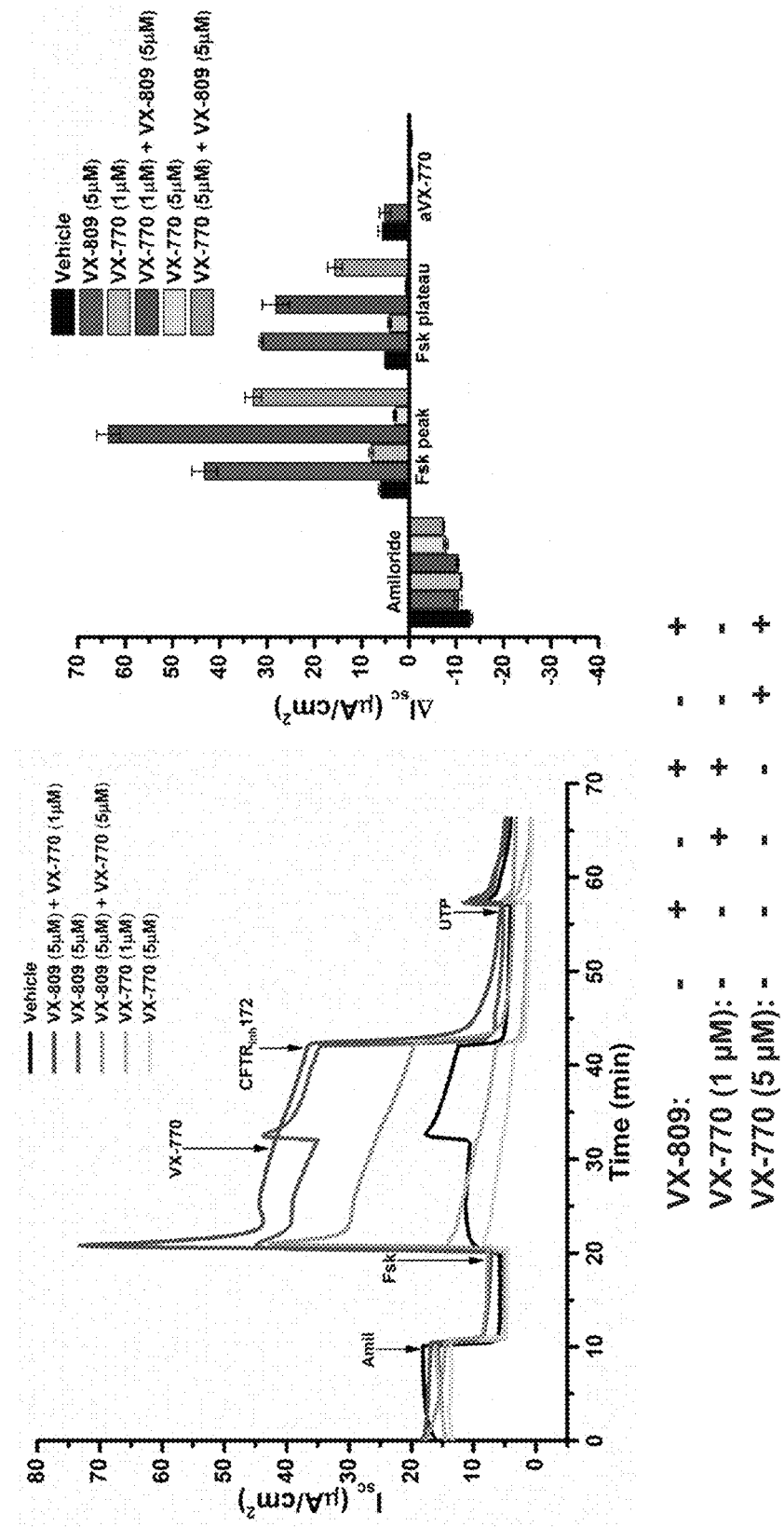
FIG. 4 shows that P67L is a CFTR processing/conductance mutation. CFTR in P67L/ΔF508 HBE is efficiently rescued by VX-809 alone or VX-809/VX-770 combination treatment. The forskolin peak is highest with VX-809 plus a lower dose of VX-770 (1 μM).
Figure 4:
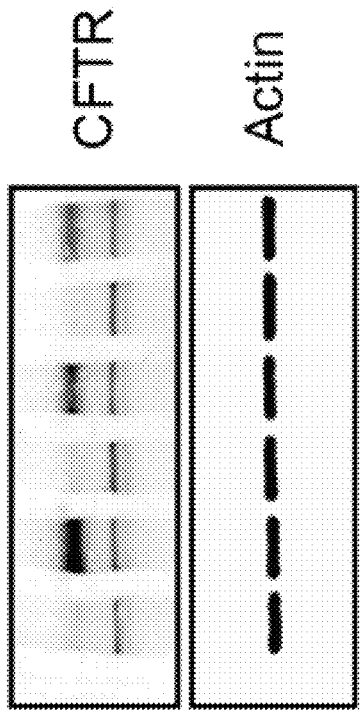

P67L is a processing/conductance mutation. CFTR in P67L/ΔF508 HBE is efficiently rescued by VX-809 alone or VX-809/VX-770 combination treatment. The forskolin peak is highest with VX-809 plus a lower dose of VX-770 (1 μM) (FIG. 4).

Figure 5:
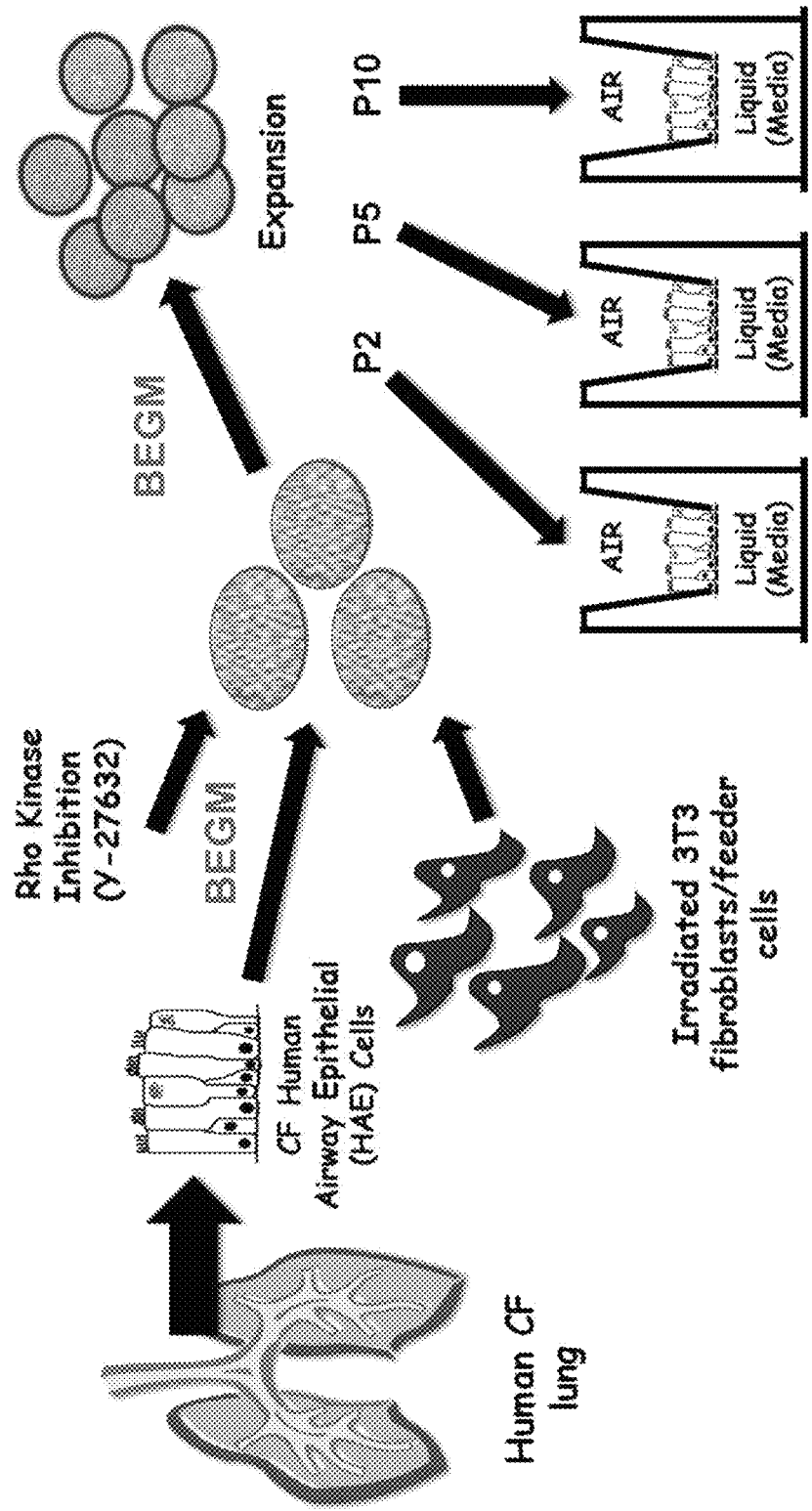
FIG. 5 shows that conditionally reprogrammed cultures (CRC) allow for expansion of cells with a specific mutation. Rescue of ΔF508/ΔF508 in CRC HBE cultures by VX-809 is maintained over high passage numbers.
Figure 5:
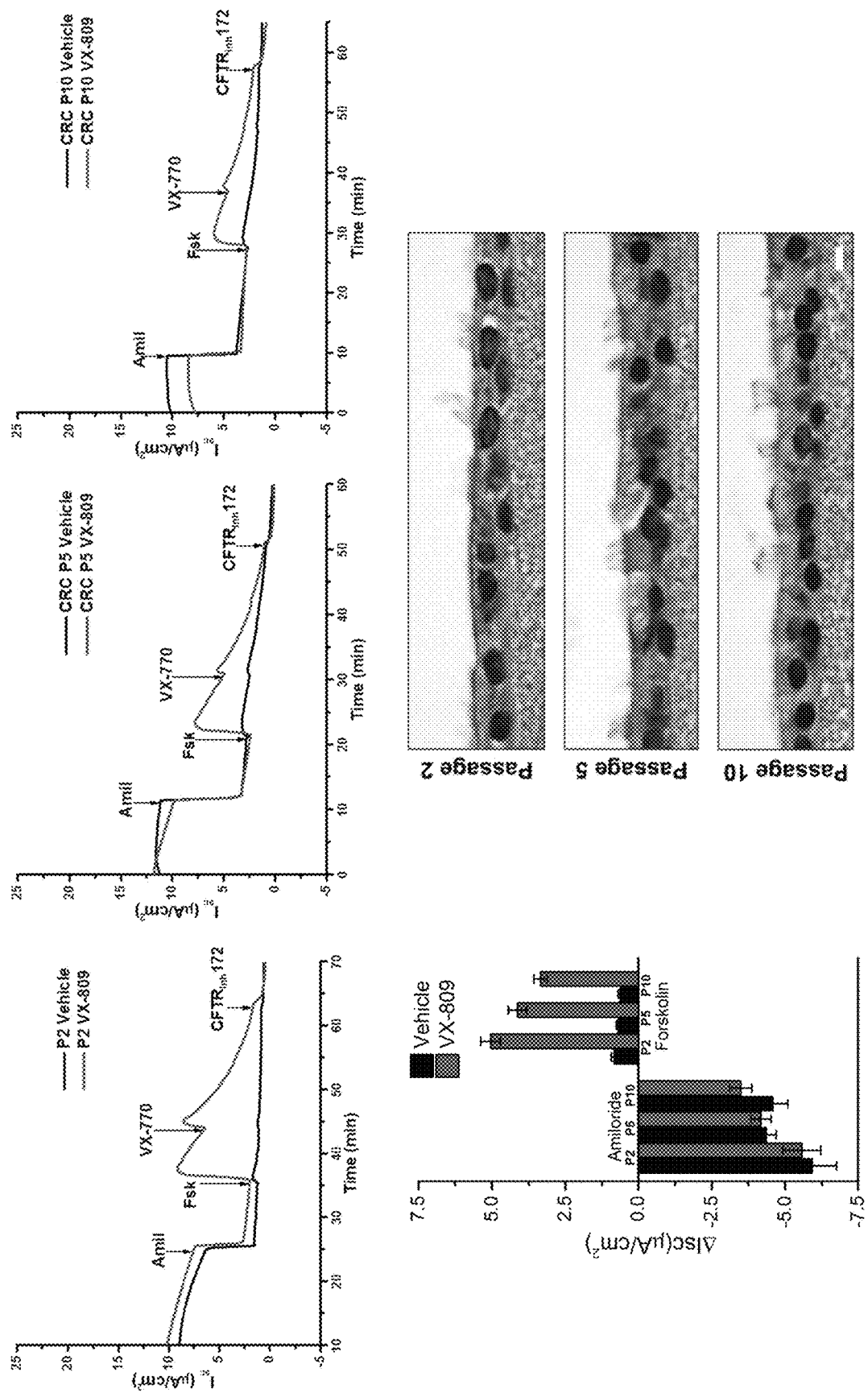

Conditionally reprogrammed cultures (CRC) allow for expansion of cells with a specific mutation. Rescue of ΔF508/ΔF508 in CRC HBE cultures by VX-809 is maintained over high passage numbers (FIG. 5).

Figure 6:
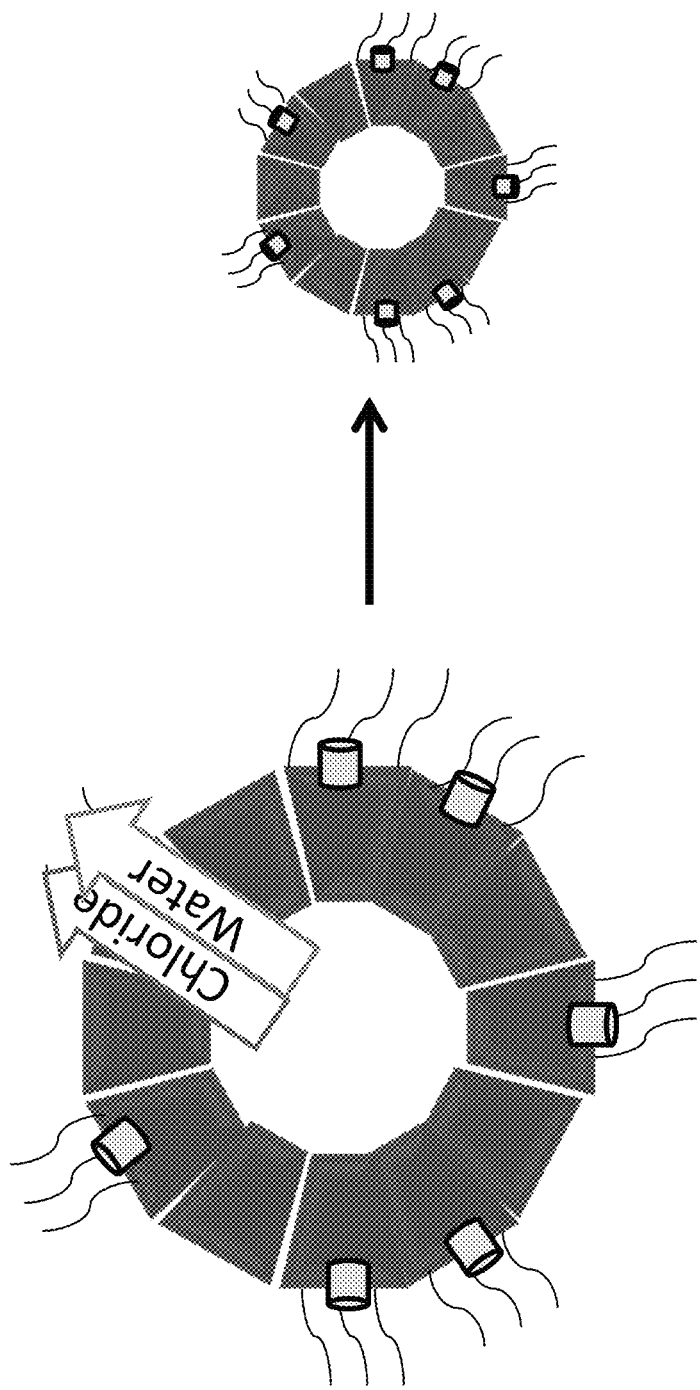
FIG. 6 shows that 3D spheroid cultures from nasal and bronchial tissue (nasospheres and broncho spheres) can form in two orientations, outward facing spheres or inward facing spheres. When CFTR is active, outside-facing spheres shrink, and inside-facing spheres swell.
Figure 6:
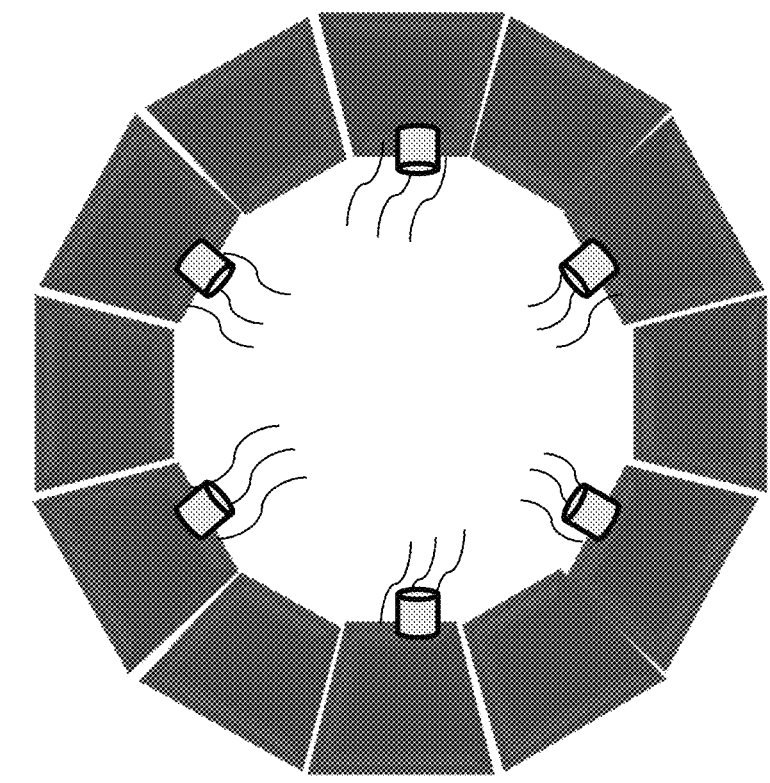
Figure 6:
Figure 6:
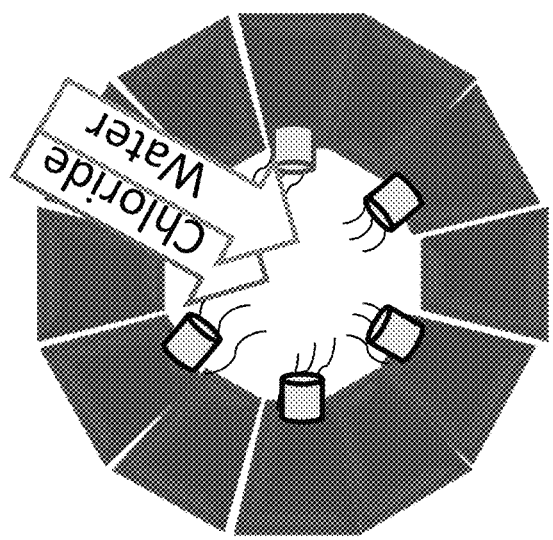

3D spheroid cultures from nasal and bronchial tissue (nasospheres and bronchospheres) can form in two orientations, outward facing spheres or inward facing spheres. When CFTR is active, outside-facing spheres shrink, and inside-facing spheres swell (FIG. 6).

Figure 7D:
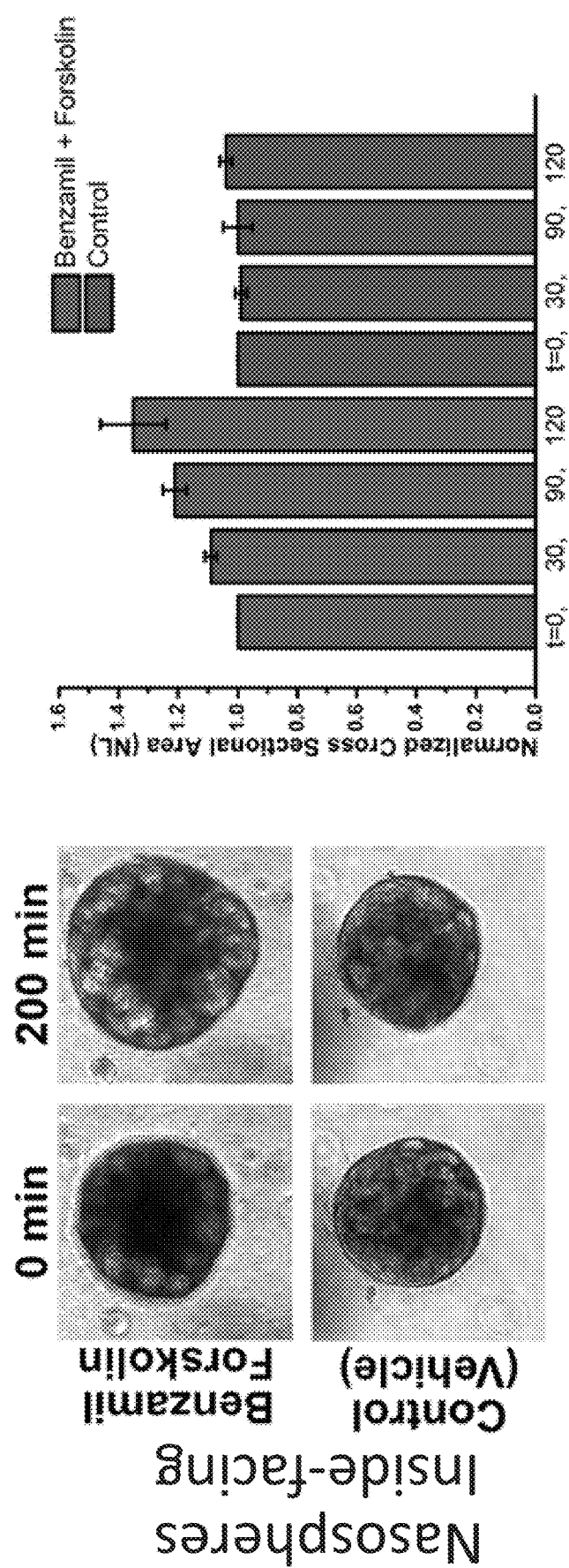
Figure 7E:
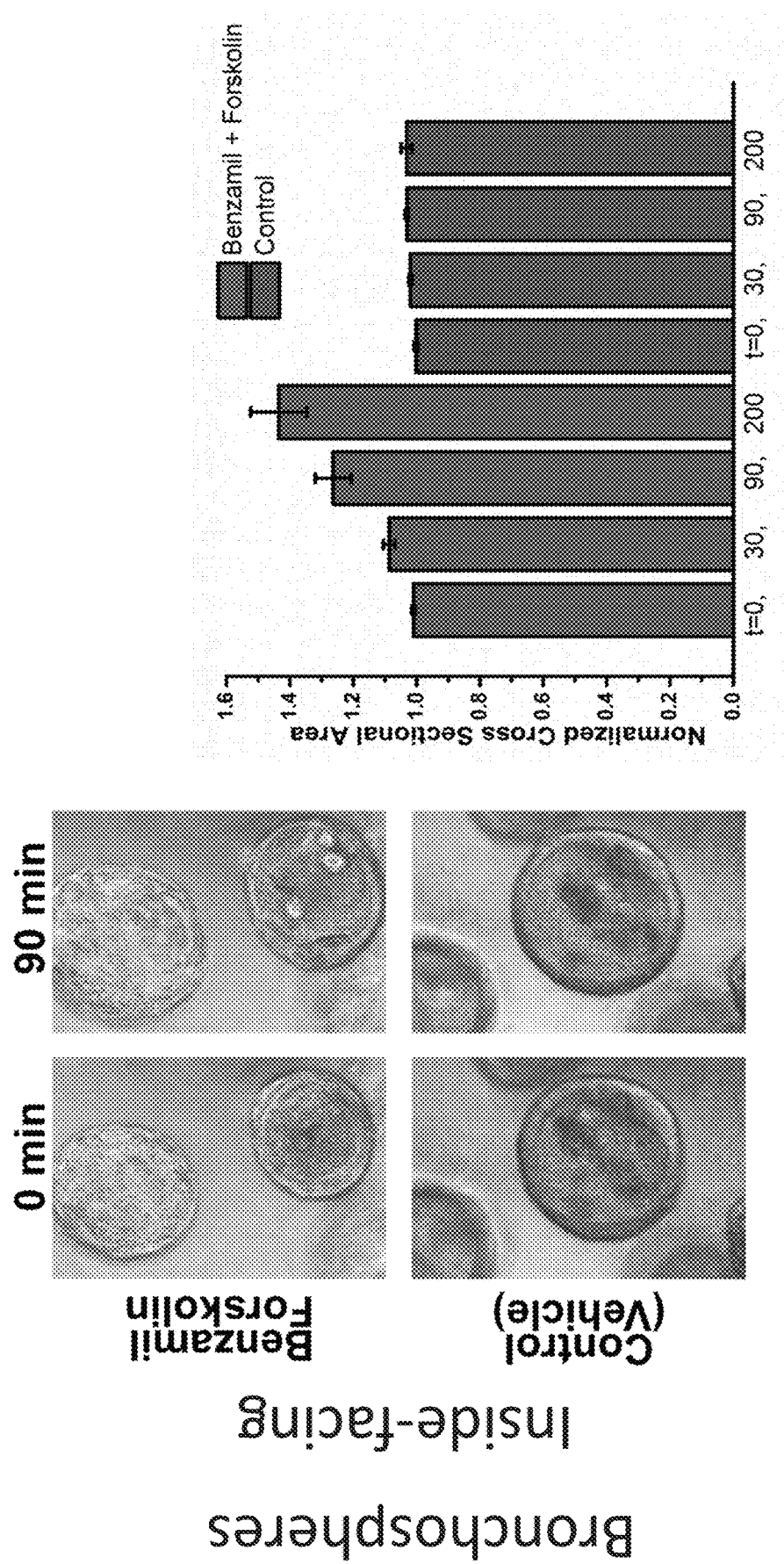

Outward facing nasospheres from nasal tissue with functional CFTR (FIG. 7A) can be seen to shrink (FIG. 7C), whereas outward facing nasospheres from a subject with CF (FIG. 7B) fail to shrink (FIG. 7C). Inward facing nasospheres with functional CFTR can be seen to swell with the addition of benzamil and forskolin (FIG. 7D). Inward facing bronchospheres with functional CFTR can be seen to swell with the addition of benzamil and forskolin (FIG. 7E).

These results demonstrate that HBE with various CFTR mutations respond differently to compounds VX-809 and VX-770, even if the mutations are in the same class. Conditionally reprogrammed cultures can provide a means to expand cells of a defined mutation. 3D spheroid cultures can allow for the testing of various compounds using cells derived from individual patients. Using these methods, compounds can be tested to identify therapeutics that are most effective for each patient.

Example 2

CFTR Rescue Affects Secreted Mucins and Mucus

Cystic fibrosis (CF) airways are characterized by mucus hyperproduction, increased mucus solids concentration and mucus plugging. Consequently, mucociliary clearance, a key element of effective host defense, is severely impaired in CF. The detailed relationship between CFTR function and properties of mucus remains poorly understood. The objective of this study was to determine whether rescued CFTR function directly impacts the secretion of mucins, the main component of mucus, and/or the biophysical properties of mucus.

Results

Figure 8A:
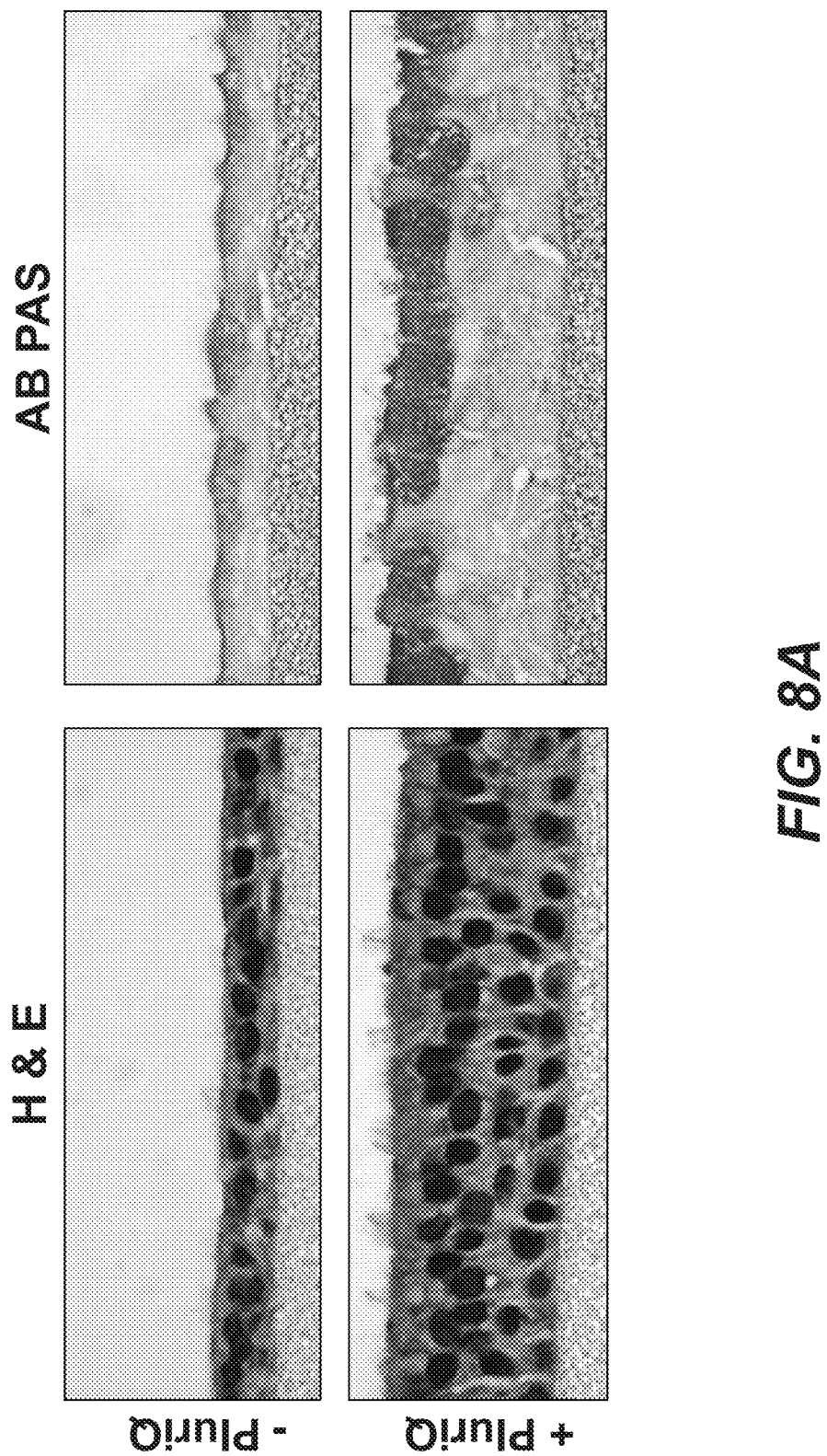
FIGS. 8A-8C show that PluriQ enhances mucus production in HBE cultures. HBE cells were maintained in UNC ALI medium +/−2% PluriQ. H & E and AB PAS staining (FIG. 8A). Immunostaining of MUCSAC and 5B with Abs 45M1 and sc-20119 Ab, respectively (FIG. 8B). Western blotting of MUCSAC using Ab 45M1 (FIG. 8C).
Figure 8C:
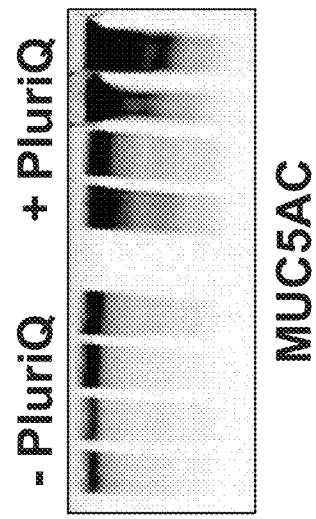
Figure 8B:
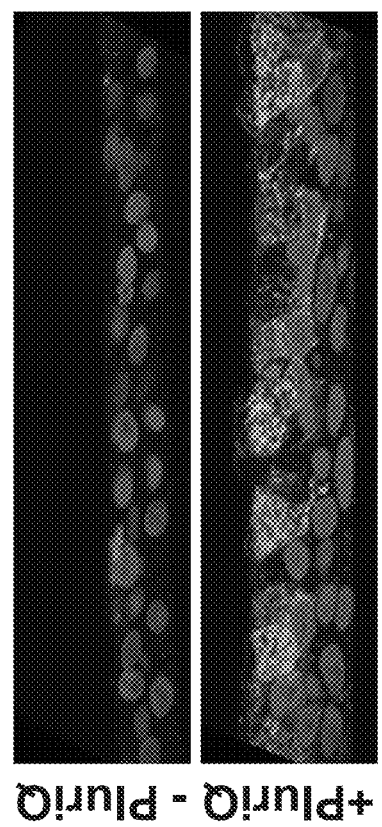

Restoration of mutant CFTR function can normalize aberrant mucus characteristics in CF airways. CF primary human bronchial epithelial (HBE) cultures were grown on Millicell supports in the presence of serum substitute PluriQ, which altered airway physiology and mucin production (FIGS. 8A-8C). Culture height and ciliation increased significantly, and mucin production was augmented. These new culture conditions generated a suitable model to study changes in mucus properties induced by CF therapies such as correctors and potentiators. Next we evaluated the impact of CFTR rescue on mucin and mucus properties. It was found that MUCSAC levels in apical washes of G551D/ΔF508 CF HBE cultures were significantly decreased following rescue with VX-770 (FIGS. 9A-9D). The viscoelastic characteristics of secreted mucus differ in CF and normal (NL) HBE cells (Hill et al. PLoS One 2014, 9:e87681). Rescue of CFTR function in P67L/ΔF508 CF HBE cells by treatment with VX-809 and/or VX-770 altered viscoelastic properties of CF mucus (FIGS. 10A-10D). In addition, we noticed that the ciliary beat frequency (CBF) of broncho spheres, which is affected by CFTR-regulated mucus viscoelasticity, is decreased in CF bronchospheres when compared to NL bronchospheres (FIGS. 10A-10D). This indicates that CBF of bronchospheres can be used as a biomarker to study effects of CFTR rescue in this culture system.

PluriQ enhances mucus production in HBE cultures. HBE cells were maintained in UNC ALI medium +/−2% PluriQ. H & E and AB PAS staining (FIG. 8A) Immunostaining of MUCSAC and 5B with Abs 45M1 and sc-20119 Ab, respectively (FIG. 8B). Western blotting of MUCSAC using Ab 45M1 (FIG. 8C).

Figure 9A:
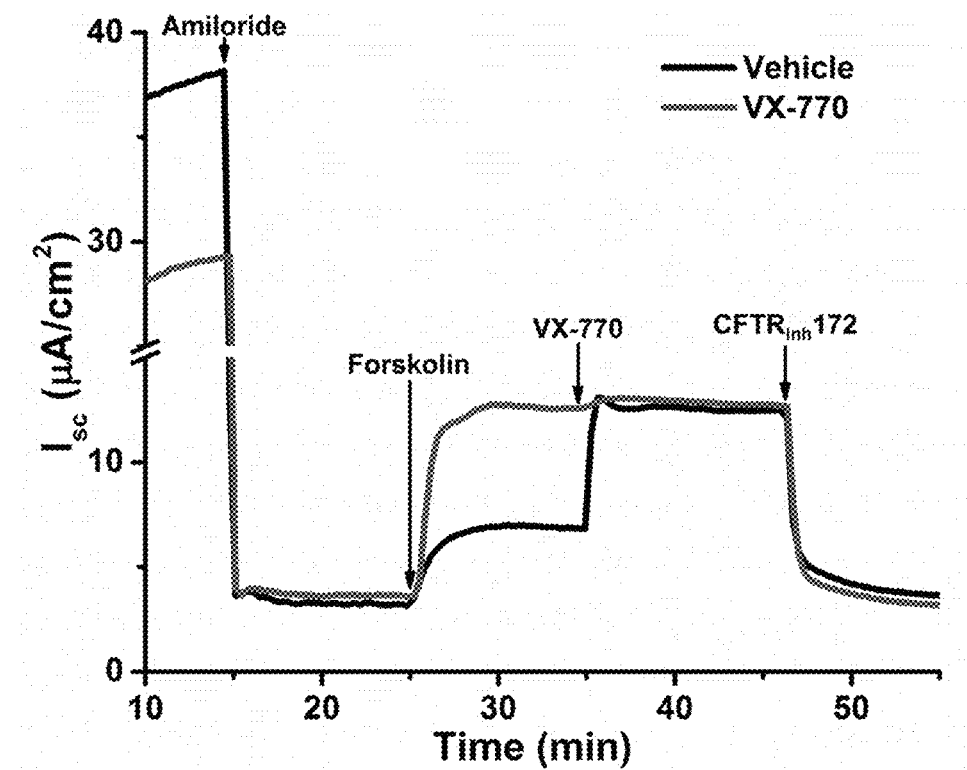
FIGS. 9A-9D show that CFTR rescue reduces MUC5AC levels in CF HBE cells. CFTR function in G551D/ΔF508 CF HBE cells cultured in ALI with PluriQ was rescued by treatment with VX-770 (5 μM, 48 hrs).
Figure 9B:
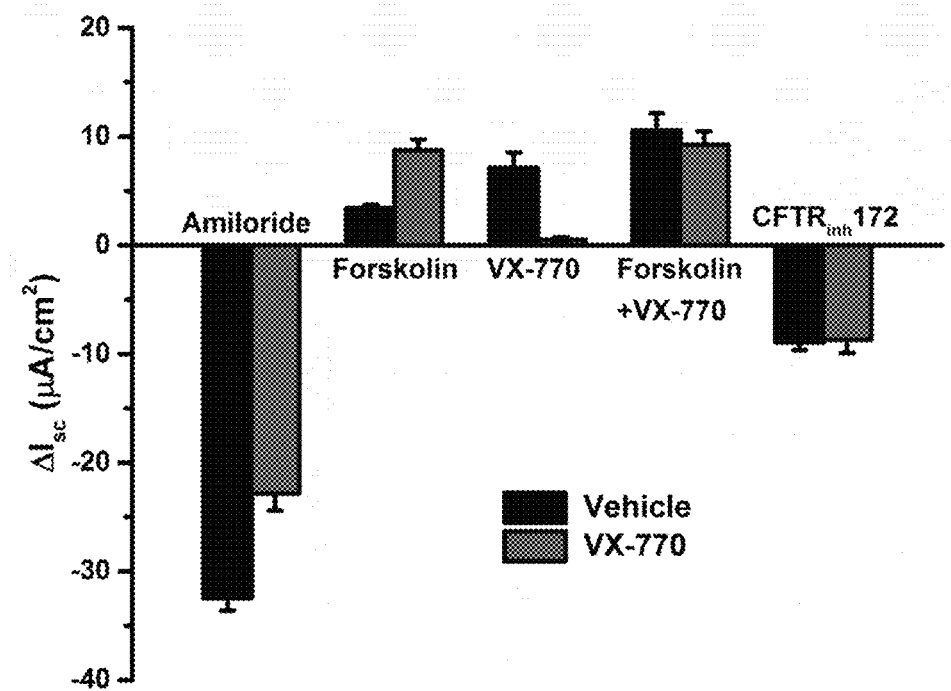
Figure 9C:
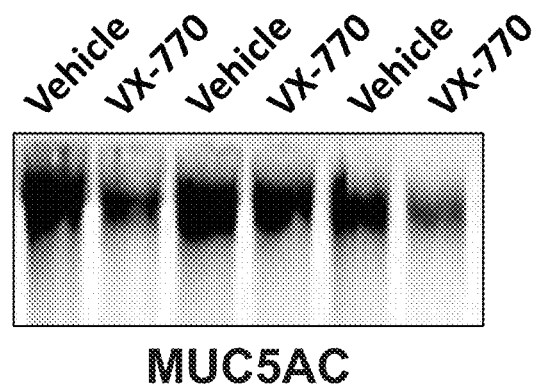
Figure 9D:
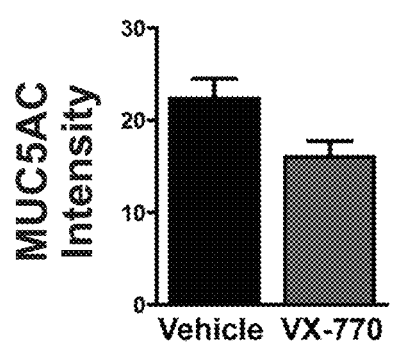

CFTR rescue reduces MUCSAC levels in CF HBE cells. CFTR function in G551D/ΔF508 CF HBE cells cultured in ALI with PluriQ was rescued by treatment with VX-770 (5 μM, 48 hrs). Representative short-circuit current (Isc) traces measured in Ussing chambers (FIG. 9A). Isc responses to amiloride, forskolin, VX-770, and CFTR-Inh172 (N=3) (FIG. 9B). MUCSAC Western blotting. D. The intensity of the MUCSAC signal is diminished in VX-770-rescued cultures (FIG. 9C).

CFTR rescue affects viscoelastic properties of mucus. (Gianotti et al. 2015, Pharmacological rescue of mutant CFTR protein improves the viscoelastic properties of CF mucus, J Cyst Fibros. Epub ahead of print; Chaudhry et al. 2015 "CFTR Rescue Affects Secreted Mucins and Mucus.", 29th Annual North American Cystic Fibrosis Conference, Phoenix, Ariz., October 2015. Pediatric Pulmonology Supplement 41 p 224). Microrheology using particle-tracking techniques demonstrated that mucus collected from CF HBE cultures was less elastic and less viscous when cells were treated with VX-809. Thus while elastic and viscous moduli are higher in CF mucus than in non-CF mucus, rescue of CFTR improves significantly CF mucus properties.

Figure 10D:
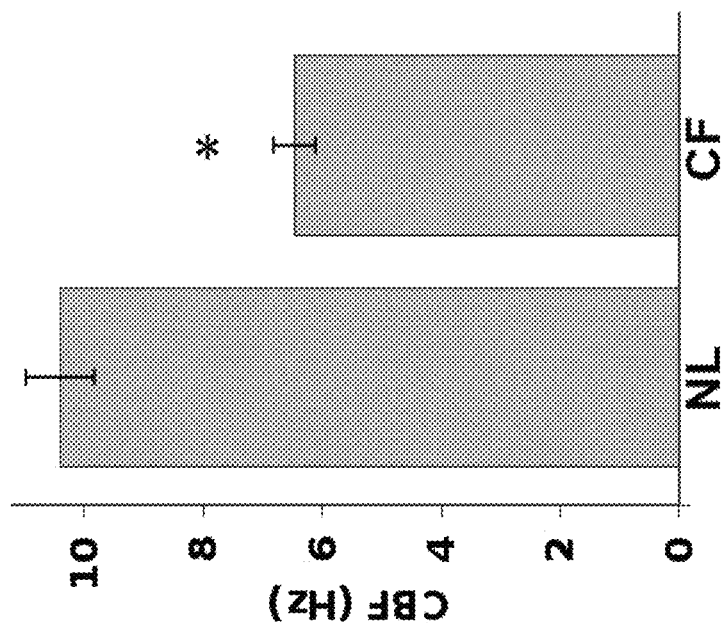
Figure 10C:
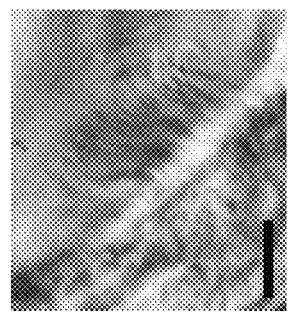

Bronchospheres produce mucus, and when CFTR function is lost, ciliary beat frequency is diminished. Primary normal (NL) and P67L/ΔF508 CF bronchial spheres grown in matrigel with the apical surface facing the inside. Sections were stained with H & E or AB PAS (Bars=100 μm) (FIG. 10A). B. AB PAS staining of NL and CF bronchospheres at different magnifications. (Bars=100 μm) (FIG. 10B). Cilia of a bronchosphere (Bar=5 μm) (FIG. 10C). NL and ΔF508/ΔF508 CF bronchospheres with beating cilia were analyzed to determine cilia beat frequency (CBF) (FIG. 10D). The graph shows average CBF from NL and CF spheres (N=6). CBF in NL spheres (10.4±1.4 Hz) was significantly faster than in CF spheres (6.5±0.9 Hz) (P=0.0002).

These results demonstrate that PluriQ supplement enhances mucus production and therefore facilitates mucins/mucus studies in HBE cells. CFTR rescue decreases MUC5AC levels in apical secretions of CF HBE cells. CFTR rescue affects the viscoelastic properties of mucus. Mucus that accumulates in the lumen of bronchospheres affects CBF, which is lower in CF than in NL spheres. Pharmacological rescue of CFTR modulates levels of secreted mucins and the biophysical properties of mucus and thus may restore mucin homeostasis in CF airways.

Example 3

Airway Sphere Assay Overview

Measuring Airway Sphere (Nasosphere and Bronchospheres) Volume Changes as Predictors of Personalized CFTR Modulator Responses.

Modified assays can be applied to measure function of other apical ion channels (Epithelial sodium channel, ENaC, and Calcium-activated chloride channel, CaCC).

Two nasosphere and bronchosphere orientations can be selectively created applying the developed protocols: "apical membrane out" (AMO) spheres that shrink in response to CFTR activation and "apical membrane in" (AMI) spheres that swell in response to CFTR activation. Our developed assays measure dose-dependence, rate and magnitude of CFTR-mediated volume changes in both formats and permit to correlate the results with clinical outcomes.

Measuring Cilia Activity in Sphere Mucus as Predictors of Mucus Properties and as Predictor of Personalized CFTR Modulator Responses.

Modified assays can be applied to measure change of mucus properties in other diseases (Asthma, COPD, etc.) or impact on hydration of other ion channels (e.g. ENaC, CaCC).

Altered mucus properties are critical in the pathogenesis of airway disease. The effect of mucus viscoelasticity on cilia activity are measured in "apical membrane in" (AMI) spheres and in AMO spheres that are cultured in a very small volume of media. Measuring cilia beat frequency (CBF) following CFTR modulator therapies may predict clinical outcome of this treatment.

Adaption to High-Throughput Format.

These assays may be expanded to high-throughput format by creating spheres (e.g. nasospheres and bronchospheres) from conditionally reprogrammed cells (CRC) (Liu, X. et al. 2012. ROCK inhibitor and feeder cells induce the conditional reprogramming of epithelial cells. Am. J. Pathol. 180, 599-607).

Example 4

Cell Culture Protocols

Protocol to Obtain Nasal Scrape Biopsies:

Nasal scrape biopsies are obtained from consented donors under approved IRB protocol. Briefly, the inferior surface of the middle turbinate of each naris is visualized with an otoscope and curettaged using a plastic curette (Rhino-probe). Biopsies are gently dislodged from the curette, collected in a conical centrifuge tube in either RPMI 1640 or Lactated Ringer's Solution and kept on ice until processing. Tissue and cells are centrifuged at 1000 rpm for 5 minutes at 4° C., and collection medium is aspirated from the cells and tissue. The tissue is suspended in BEGM containing 1 mg/mL DNase1 at room temperature for 20 minutes. The nasal tissue is then washed with BEGM, centrifuged at 1000 rpm at 4° C., and the supernatant is removed.

Protocol to Obtain AMO Spheres (in Media)/Sphere Formation from Primary Non-Adherent Cells:

AMO (apical membrane out, cilia outside, outside-facing, epithelial cells facing the outside) spheres forming on cultured epithelial cells are collected from the media on days 2-7. They are maintained in low attachment plates in BEGM. Tissue and cells are seeded onto a PureCol coated tissue culture dish in a MINIMAL volume (200 uL) of BEGM plus antibiotics. Nasal explants are observed daily, and 200 uL of BEGM Medium is added to the culture at 24 and 48 hours. Floating AMO spheres typically form in the supernatant of cultures of non-disrupted epithelia tissues in minimal volume media 2-5 days after the initial sample collection. The tissue remains attached to the surface of the culture dish to allow cell growth from the explant. On days 3-7, self-assembling AMO spheres are collected by pipette from the explant culture and placed into a low attachment culture plate. Non-adherent cells are also collected every 24 hours and placed into a separate well in the same low attachment culture plate for further sphere development. Media sphere assays are performed at 7-28. Spheres can be maintained for up to 4 weeks by collection with large-bore pipets and gentle centrifugation. They are resuspended in BEGM and seeded into low attachment plates.

Protocol to Obtain Nasal AMI Spheres (in Matrigel):

AMI (apical membrane in, cilia inside, inside facing, epithelial cells facing the inside) spheres form in Matrigel from conditionally reprogrammed expanded epithelial cells. The epithelial cells obtained in the nasal scrape biopsy are grown on the PureCol coated TC dish for 3-4 days in BEGM. Irradiated feeder cells are added to the TC dish and cells are co-cultured in F Media+Y compound. Epithelial cells are expanded and passaged. They can be further expanded using the co-culture method. The cells can also be seeded in Matrigel and ALT media to allow for the formation of AMI spheres. AMI spheres are formed from expanded adherent nasal epithelial conditionally reprogrammed cells (CRC). AMI spheres are seeded in matrigel at passage 1 (P1) and higher. Conditionally reprogrammed cells (CRC) are passaged using 0.1% Trypsin/EDTA when colonies reach 70-90% confluence. Upon passage, CRC nasal epithelial cells are further expanded with irradiated mouse 3T3 J2 fibroblasts and F Media+Y compound. The cells are then seeded in matrigel to form AMI nasospheres. On ice, ~1-5× $10^3$ CRC P1 cells (nasospheres are seeded at 2400 cells per 6.5 mm transwell or at 5000 cells per 12 mm millicell, bronchospheres are seeded at 1200 cells per 6.5 mm transwell or at 3600 cells per 12 mm millicell) are suspended in 100 μL matrigel solution (made as a 1:3 dilution in ALI Medium) per 6.5 mm transwell culture inserts or in 300 μL matrigel solution (made as 1:3 dilution in ALI Medium) per 12 mm millicell. A base of collagen-containing semi-solid matrix mixed with ALI at 1:2 is applied to the insert prior to cell seeding. The base is allowed to solidify at 37° C. for 30 minutes-1 hour. The inserts are seeded with 100 uL or 300 μL matrigel and cell suspension, and are placed at 37° C. to allow the matrigel to set for 30 minutes-1 hour. ALI medium is added basolaterally, and replaced every 2 days in culture. Spheres are assayed from 3-6 weeks following formation e.g. If required, Sphere forming efficiency can be increased by co-seeding of embryonic feeder cells (e.g. 1200 bronchial epithelial cells+24,000 MRC5s in Matrigel per 6.5 mm transwell).

General Culture Protocol to Obtain CRC Cells for Sphere Formation:

After 3 days in culture, nasal primary cells are expanded using an adaptation of the CRC method for sphere formation (Liu, X. et al. (2012) "ROCK inhibitor and feeder cells induce the conditional reprogramming of epithelial cells" *Am. J. Pathol.* 180, 599-607). Irradiated mouse 3T3 J2 fibroblasts are added directly to the culture dish containing the primary cells. The cells are grown in F Media+Y compound. When colonies reached 70-90% confluence, the CRC culture is washed with 1×DPBS and passaged using 0.1% Trypsin/EDTA solution. Subsequent passages are further expanded on 3T3J2 fibroblasts and co-cultured in the presence of F Media+Y Compound. CRC cells are seeded at high density in low attachment plates in BEGM to form AMO spheres or at low density in matrigel as described to form AMI spheres. CRC AMO and AMI spheres require several weeks to differentiate.

Protocol to Process Bronchial Tissue:

To obtain bronchial epithelia cells, bronchial biopsies can be isolated from explanted lungs. Bronchial tissue may also be obtained from patients undergoing bronchoscopy. Briefly, tissue is digested with 1% Protease/DNase solution overnight with gentle rocking at 4° C. Epithelial cells are dissociated by gentle scraping using a scalpel. Cells are then collected and FBS is added to quench the Protease. For our purposes, a sample of cells is obtained at this point in the processing (we refer to these as P cells: Protease).

AMO and AMI Bronchospheres:

A small aliquot of Protease digested cells (P) is seeded into one well of a 24 well low attachment plate in BEGM plus 1× antibiotics and antifungals. Primary AMO media bronchospheres will be obtained from this sample. The remaining primary epithelial cells are seeded onto a PureCol coated tissue culture dish in BEGM plus 1× antibiotics and antifungals and allowed to grow. Nonadherent epithelial cells and bronchospheres are collected by gentle washing of the tissue culture plate at 24, 48 and 72 hours after seeding. Following centrifugation at 400 rpm, cells and bronchospheres are seeded into an appropriate number of wells of the 24 well low attachment plates. These media AMO bronchospheres are fully developed (visible lumen present) within a few days.

Once adherent bronchial cells reach confluence, cells are passaged using 0.1% Trypsin/EDTA solution. Bronchial epithelial cells are seeded as both AMO and AMI spheres, as well as expanded in CRC method as described for nasal cells. Accordingly, passage 1 epithelial cells are seeded into the low attachment plate in BEGM to allow for the formation of AMO media spheres. Cells are also seeded into matrigel (as described for nasal cells) for generation of AMI bronchospheres. Epithelial cells can also be cultured in the CRC method for expansion beginning at day 3 after initial plating or at passage 1. These cells can then be used to generate both AMO and AMI spheres.

Example 5

Sphere Assay Protocols

Shrinking and Swelling Assays:

AMO spheres shrink when CFTR is activated whereas AMI spheres swell (FIGS. 6, 7A-7E). Spheres are directly visualized with confocal microscope system with an environmental chamber (temperature, $CO_2$, humidity control). Then CFTR is for example measured by addition of benzamil (to inhibit ENaC) and forskolin or forskolin/IBMX (to activate CFTR). The cross-sectional area of spheres (or alternatively diameter) is quantified using an Image analysis program (e.g. Image J). Movement of AMO spheres in media may occur and can be restricted by applying small volumes of surrounding media or antibody coated plates that bind to external epitopes of surface protein (membrane-associated mucins MUC1).

Cilia Activity Measurements:

The AMI sphere cultures will be taken from the incubator, placed on the microscope stage in an temperature controlled environmental chamber. A Nikon TE2000 inverted microscope using a 20×ELWD objective and phase optics is used. Videos are taken with a Roper ES310-T camera at 60 frames per second under the control of SAVA software18. At least 10 spheres are chosen at random from each culture and 5 videos are taken for each nasosphere. Measurement of CBF is performed post-capture with SAVA in whole field analysis mode. Data were obtained so far with AMI spheres (FIGS. 10A-10D). AMO spheres grown in a small volume of media may be analyzed in a similar fashion.

Immobilizing Spheres with Cilia Facing the Outside (AMO Spheres):

Due to outward facing cilia and cilia activity, AMO spheres may move if they are not immobilized, making analysis of shrinking or swelling more difficult. To immobilize AMO spheres, first, spheres are incubated with antibodies that detect and bind to extracellular epitopes. For example, for nasal and bronchial spheres, antibodies detecting the extracellular Mucin domain of Transmembrane Mucins, (e.g. Muc1 antibody binding to extracellular Muc1 domain) can be used. Antibodies bind epitopes on spheres. Second, spheres are washed and transferred to Protein A, G, or A/G, and L coated microplates or dishes (commercially available). Antibodies bound to spheres will be captured by Protein A, G, or A/G that is tethered to the coated microplates or dishes. Optionally, should any non-bound spheres be present, they can be removed by washing. These immobilized spheres can now be utilized for shrinking/swelling assays.

Example 6

Measurement of Ion Channel Function

Drug Treatments in Assays to Measure CFTR Function:
1. ENaC is inhibited with ENaC inhibitor compound (e.g. with benzamil or amiloride)
2a) CFTR is activated by CFTR activator (e.g. with forskolin or other compound that increases cAMP or activates CFTR otherwise)
2b) alternatively to 2a: Steady state CFTR activity may be measured by adding CFTR inhibitor.

Assay Outcome:

AMO spheres will shrink, whereas AMI spheres will swell.

Drug Treatments in Assays to Measure ENaC Function:

1. CFTR is inhibited with CFTR inhibitor compound (e.g. with CFTR inhibitor-172 or GlyH101 etc.)
2. ENaC function is modulated (e.g. with cAMP, $PIP_2$ and $PIP_3$ activation, inhibition of proteases, ENaC inhibitors etc.)

Assay Outcome:

AMO spheres will swell, whereas AMI spheres will shrink.

Drug Treatments in Assays to Measure CaCC Function:

1. Inhibit ENaC (e.g. with benzamil, amiloride etc.) and CFTR (e.g. with CFTR inhibitor-172, GlyH101 etc.)
2. Activate CaCC (e.g. with UTP or other means modulate calcium concentrations etc.)

Assay Outcome:

AMO spheres will shrink, whereas AMI spheres will swell.

Additional Measurements

The malfunctioning of proteins that regulate CFTR, ENAC and CaCC may be detected by these assays. For example, malfunctioning proteins that regulate CFTR, ENAC and CaCC can result in altered channel activity, which can be detected by these assays.

Example 7

Assay Examples

Shrinking of Nasospheres and Swelling of Nasospheres Following Activation of CFTR AMO and AMI Nasospheres Respond to CFTR Activation.

Non-CF (NL) and CF nasal epithelial cells were obtained via curette biopsy of the inferior turbinate and were cultured to form AMO 3D nasospheres. AMO nasospheres in suspension polarize, with cilia and the apical plasma membrane on the outside as shown, e.g., in FIG. 7A. Nuclei were stained with DAPI and the plasma membrane and cilia were stained using CellMask Plasma Membrane Stains. NL AMO nasospheres express CFTR at the apical membrane as shown by CFTR immunostaining on PFA fixed and permeabilized AMO nasopheres as shown, e.g., in FIG. 7B. When treated with amiloride to inhibit ENaC and forskolin to activate CFTR, NL but not CF (ΔF508/ΔF508) Calcein Green-stained nasospheres showed volume shrinkage (Bar=50 µm), and quantitation of NL nasosphere shrinkage as shown, e.g., in FIG. 7C. NL AMI nasospheres showed volume increase when ENaC is inhibited with benzamil (BA) and CFTR is activated with forskolin (FSK), and quantitation of NL nasosphere swelling as shown, e.g., in FIG. 7D.

Swelling of AMI Bronchospheres Following Activation of CFTR

CF and Non-CF (NL) HBE Cells from AMI 3D Bronchospheres when Seeded as Single Cells in Matrigel.

NL AMI bronchospheres swell after benzamil (BA) pretreatment and stimulation with forskolin (FSK), and quantitation of swelling of AMI spheres from 3 donors, as shown, e.g., is FIG. 7E.

AMI Bronchospheres Produce Mucus and CBF is Decreased in CF Versus Normal, Rescue of CFTR Function Will Increase CBF in CF Spheres Bronchospheres Produce Mucus, and when CFTR Function is Lost, Ciliary Beat Frequency is Diminished.

Primary normal (NL) and P67L/ΔF508 CF bronchial spheres grown in matrigel with the apical surface facing the inside and are shown in FIG. 10A. Sections were stained with H & E or AB PAS (Bars=100 µm). Cilia of bronchosphere (Bar=5 µm) are shown in FIG. 10C. NL and ΔF508/ΔF508 CF bronchospheres with beating cilia were analyzed to determine cilia beat frequency (CBF), as shown in the graph in FIG. 10D. The graph shows average CBF from NL and CF spheres (N=6). CBF in NL spheres (10.4±1.4 Hz) was significantly faster than in CF spheres (6.5±0.9 Hz) (P=0.0002).

Swelling of AMI CF Bronchospheres is Restored after Rescue of Mutant CFTR Protein with CFTR Corrector VX-809 (Lumacaftor)

AMI Bronchospheres from CF Patients Swell when Treated with CFTR Modulators.

Figure 11A:
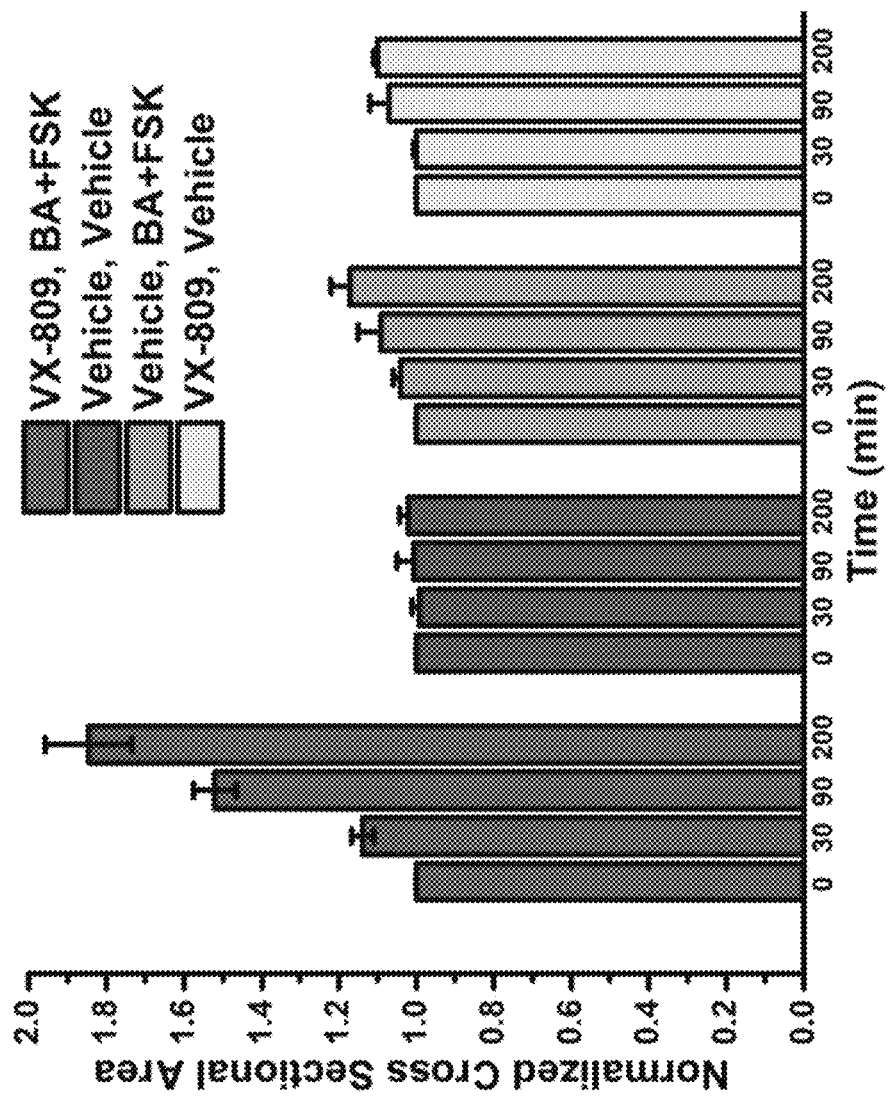
FIGS. 11A-11C show that inward facing bronchospheres from CF patients swell when treated with CFTR modulators. Bronchospheres cultured from CF HBE cells (P67L/ΔF508) were treated chronically with vehicle or corrector VX-809 and then acutely with vehicle or forskolin plus benzamil (aFsk/Benz) (FIG. 11A). Treatment with VX-809 and Fsk/Benz resulted in swelling of bronchospheres, indicating that the mutant CFTR was successfully rescued and is a functional channel. Responses observed with VX-809 treatment correlated with restored CFTR function as measured in CF HBE (P67L/ΔF508) 2D cultures in Ussing chambers (FIG. 11B). VX-809 promoted formation of mature band of CFTR in CF HBE cells (P67L/ΔF508) as detected by Western blotting (FIG. 11C).
Figures 11B, 11C:
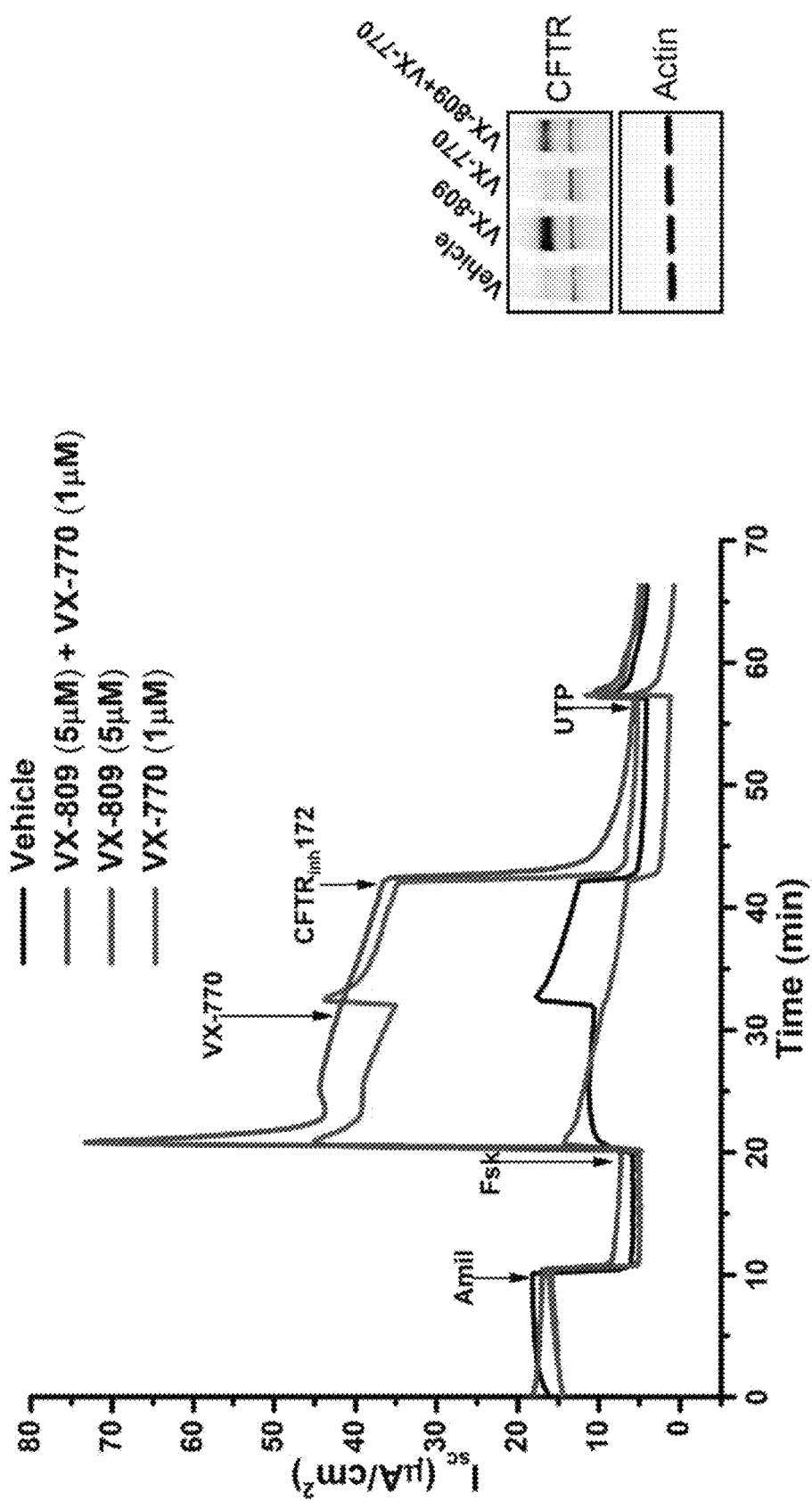

AMI bronchospheres cultured from CF HBE cells (P67L/ΔF508) were treated chronically with vehicle or corrector VX-809 and then acutely with vehicle or forskolin (FSK) plus benzamil (BA) is shown in FIG. 11A. Treatment with VX-809 and BA+FSK resulted in swelling of bronchospheres, indicating that the mutant CFTR was successfully rescued and is a functional channel. Responses observed with VX-809 treatment correlated with restored CFTR function as measured in CF HBE (P67L/ΔF508) 2D cultures in Ussing chambers, as shown in FIG. 11B. VX-809 promoted formation of mature band of CFTR in CF HBE cells (P67L/ΔF508) as detected by Western blotting, as shown in FIG. 11C.

Shrinking of AMO Nasospheres is Restored after Rescue of Mutant CFTR Protein with VX-770 (Ivacaftor)

AMO Nasospheres Respond to CFTR Activation and Modulators.

Figure 12B:
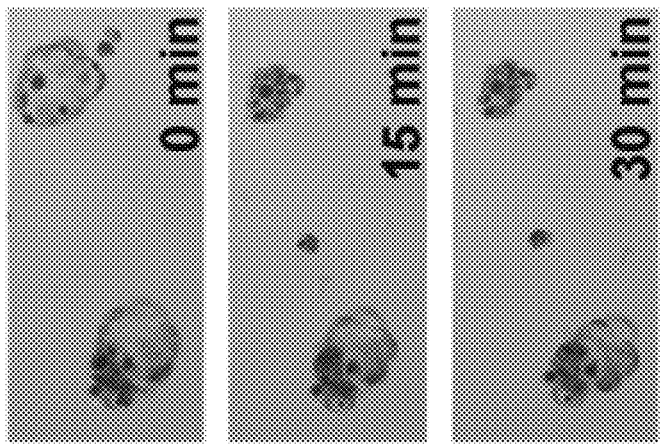
FIGS. 12A and 12B show that outward facing nasospheres from CF patients shrink when treated with CFTR modulators. When treated with amiloride to inhibit ENaC and forskolin to activate CFTR, NL, but not CF, nasospheres showed volume shrinkage (FIG. 12A). However, ΔF508/G551D nasospheres regain their shrinking behavior after treatment with VX770 (ivacaftor) (FIG. 12B). Rescue of this mutation has been confirmed by functional and biochemical rescue measurements of CFTR as well as by the success of this drug in the clinic for ΔF508/G551D patients.
Figure 12A:
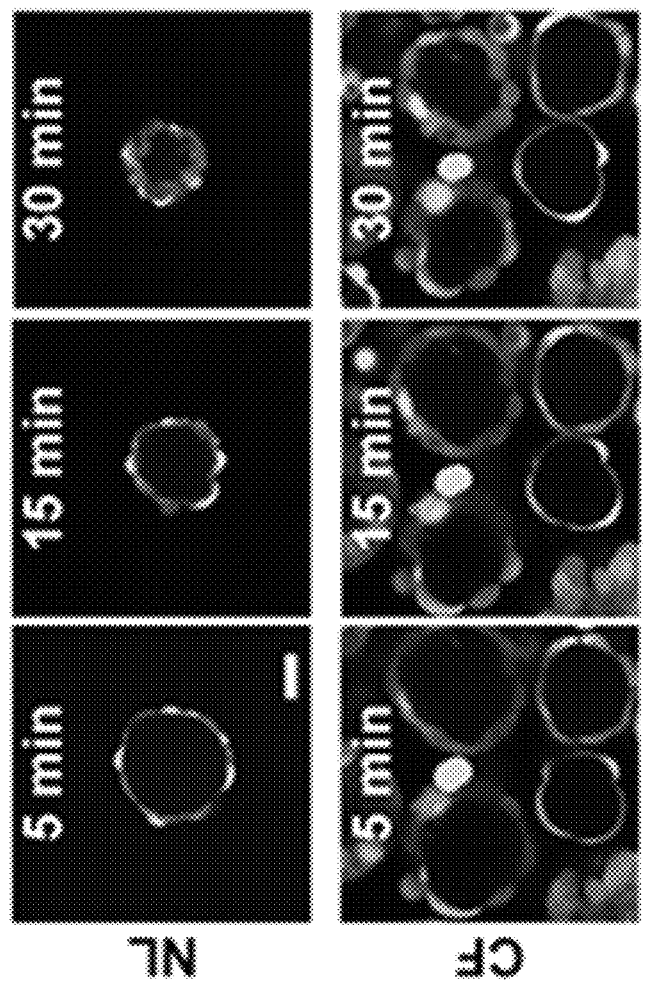

Non-CF (NL) and CF nasal epithelial cells were obtained via curette biopsy of the inferior turbinate and were cultured to form AMO 3D nasospheres. Nasospheres in suspension polarize, with cilia and the apical plasma membrane on the outside. Nuclei were stained with DAPI and the plasma membrane and cilia were stained using CellMask Plasma Membrane Stains (see, e.g., FIG. 7A). NL nasopheres express CFTR at the apical membrane as shown by CFTR immunostaining of a PFA fixed and permeabilized nasopheres (see, e.g., FIG. 7B). When treated with amiloride to inhibit ENaC and forskolin to activate CFTR, NL, but not CF, nasospheres exhibited volume shrinkage, as shown in FIG. 12A. However, ΔF508/G551D CF nasospheres regain shrinking behavior after treatment with VX770 (ivacaftor) (FIG. 12B). Rescue of this CFTR mutation has been confirmed by functional and biochemical rescue measurements of CFTR as well as by the success of this drug in the clinic for ΔF508/G551D patients.

The foregoing is illustrative of the present invention, and is not to be construed as limiting thereof. Although the invention has been described in detail with reference to various embodiments set forth herein, variations and modifications exist within the scope and spirit of the invention as described and defined in the following claims.

That which is claimed is:

1. A method of determining an ion channel response to a chemical and/or biological compound, the method comprising:
   contacting a spheroid comprising epithelial cells with the chemical and/or biological compound, wherein the spheroid produces mucus; and
   responsive to the spheroid being contacted with the chemical and/or biological compound, identifying a physiological response of the spheroid, wherein identifying the physiological response of the spheroid comprises identifying a change in the mucus, and wherein identifying the change in the mucus comprises:
measuring viscoelasticity, pH, and/or mucus solids concentration of the mucus prior to contacting the spheroid with the chemical and/or biological compound,
measuring viscoelasticity, pH, and/or mucus solids concentration of the mucus after contacting the spheroid with the chemical and/or biological compound, and
determining a change in the viscoelasticity, pH, and/or mucus solids concentration for the mucus based on the viscoelasticity, pH, and/or mucus solids concentration prior to and after contacting the spheroid with the chemical and/or biological compound, thereby determining the ion channel response of the spheroid to the chemical and/or biological compound,
wherein the spheroid comprises an interior core and an exterior surface, and a plurality of the epithelial cells have apical membranes that face towards the interior core of the spheroid.

2. The method of claim 1, wherein the spheroid comprises epithelial cells derived from a subject and the method further comprises predicting identifying the subject's ion channel response to the chemical and/or biological compound based on the ion channel response of the spheroid to the chemical and/or biological compound.

3. The method of claim 2, wherein the chemical and/or biological compound is effective for treating a channelopathy in the subject.

4. The method of claim 1, wherein the spheroid comprises epithelial cells that have been expanded in the presence of a ROCK inhibitor and feeder cells.

5. The method of claim 1, wherein identifying the physiological response of the spheroid further comprises determining a change in morphology for the spheroid.

6. The method of claim 5, wherein determining the change in morphology for the spheroid comprises:
measuring at least one morphology parameter prior to contacting the spheroid with the chemical and/or biological compound;
measuring the at least one morphology parameter after contacting the spheroid with the chemical and/or biological compound; and
calculating the difference between the at least one morphology parameter prior to and after contacting the spheroid with the chemical and/or biological compound to provide the change in morphology for the spheroid.

7. The method of claim 1, wherein identifying the physiological response of the spheroid further comprises measuring whether the spheroid shrinks or swells.

8. The method of claim 1, wherein identifying the physiological response of the spheroid further comprises:
measuring a cilia activity prior to contacting the spheroid with the chemical and/or biological compound;
measuring the cilia activity after contacting the spheroid with the chemical and/or biological compound; and
determining a change in the cilia activity for the spheroid based on the cilia activity prior to and after contacting the spheroid with the chemical and/or biological compound.

9. The method of claim 8, wherein determining the change in cilia activity for the spheroid further comprises measuring cilia dynamics and determining a change in the cilia dynamics.

10. The method of claim 9, wherein determining the change in cilia dynamics for the spheroid comprises:
measuring a first average cilia dynamics parameter prior to contacting the spheroid with the chemical and/or biological compound;
measuring a second average cilia dynamics parameter after contacting the spheroid with the chemical and/or biological compound; and
calculating the difference between the first average cilia dynamics parameter and the second average cilia dynamics parameter to provide the change in cilia dynamics for the spheroid.

11. The method of claim 9, wherein the change in cilia dynamics is an increase in cilia dynamics, and the increase in cilia dynamics is an indication that the chemical and/or biological compound will be effective in modulating a pharmacological response in a subject.

12. The method of claim 1, wherein the method is a high-throughput method.

13. The method of claim 1, wherein at least a portion of the epithelial cells are derived from a subject.

14. The method of claim 1, wherein the epithelial cells comprise airway epithelial cells, nasal epithelial cells, bronchial epithelial cells, and/or alveolar epithelial cells.

15. The method of claim 1, wherein identifying the change in the mucus comprises:
measuring viscoelasticity of the mucus prior to contacting the spheroid with the chemical and/or biological compound,
measuring viscoelasticity of the mucus after contacting the spheroid with the chemical and/or biological compound, and
determining the change in the viscoelasticity for the mucus based on the viscoelasticity prior to and after contacting the spheroid with the chemical and/or biological compound.

16. The method of claim 1, wherein identifying the change in the mucus comprises:
measuring pH of the mucus prior to contacting the spheroid with the chemical and/or biological compound,
measuring pH of the mucus after contacting the spheroid with the chemical and/or biological compound, and
determining the change in the pH for the mucus based on the pH prior to and after contacting the spheroid with the chemical and/or biological compound.

17. The method of claim 1, wherein identifying the change in the mucus comprises:
measuring mucus solids concentration of the mucus prior to contacting the spheroid with the chemical and/or biological compound,
measuring mucus solids concentration of the mucus after contacting the spheroid with the chemical and/or biological compound, and
determining the change in the mucus solids concentration for the mucus based on the mucus solids concentration prior to and after contacting the spheroid with the chemical and/or biological compound.

18. A method of determining an ion channel response to a chemical and/or biological compound, the method comprising:
contacting a spheroid comprising epithelial cells with the chemical and/or biological compound, wherein the spheroid produces mucus; and
responsive to the spheroid being contacted with the chemical and/or biological compound, identifying a physiological response of the spheroid, wherein identifying the physiological response of the spheroid comprises:
  measuring a cilia activity prior to contacting the spheroid with the chemical and/or biological compound;
  measuring a cilia activity after contacting the spheroid with the chemical and/or biological compound; and
  determining a change in cilia activity for the spheroid based on the cilia activity prior to and after contacting the spheroid with the chemical and/or biological compound, thereby determining the ion channel response to the chemical and/or biological compound,
wherein the spheroid comprises an interior core and an exterior surface, and a plurality of the epithelial cells have apical membranes and cilia that face towards the interior core of the spheroid.

19. The method of claim 18, wherein at least a portion of the epithelial cells are derived from a subject.

20. The method of claim 18, wherein the epithelial cells comprise airway epithelial cells, nasal epithelial cells, bronchial epithelial cells, and/or alveolar epithelial cells.

* * * * *

UNITED STATES PATENT AND TRADEMARK OFFICE
CERTIFICATE OF CORRECTION

PATENT NO. : 11,357,758 B2
APPLICATION NO. : 15/440720
DATED : June 14, 2022
INVENTOR(S) : Gentzsch et al.

It is certified that error appears in the above-identified patent and that said Letters Patent is hereby corrected as shown below:

In the Specification

Column 3, Line 35: Please correct "MUCSAC" to read --MUC5AC--

Column 3, Line 37: Please correct "MUCSAC" to read --MUC5AC--

Column 3, Line 45: Please correct "MUCSAC" to read --MUC5AC--

Column 3, Line 46: Please correct "MUCSAC" to read --MUC5AC--

Column 5, Line 13: Please correct "+10%" to read --± 10%--

Column 5, Line 17: Please correct "+10%, ±5%, ±1%, +0.5%" to read --±10%, ±5%, ±1%, ±0.5%--

Column 5, Line 39: Please correct "2,000" to read --2,000 μm--

Column 17, Line 33: Please correct "51251N" to read --S1251N--

Column 18, Line 29: Please correct "MUCSAC" to read --MUC5AC--

Column 18, Line 47: Please correct "MUCSAC" to read --MUC5AC--

Column 18, Line 48: Please correct "MUCSAC" to read --MUC5AC--

Column 18, Line 50: Please correct "MUCSAC" to read --MUC5AC--

Column 18, Line 56: Please correct "MUCSAC" to read --MUC5AC--

Signed and Sealed this
Eleventh Day of April, 2023

Katherine Kelly Vidal
*Director of the United States Patent and Trademark Office*

Column 18, Line 57: Please correct "MUCSAC" to read --MUC5AC--

Column 20, Line 57: Please correct "ALT" to read --ALI--